(12) United States Patent
Poole et al.

(10) Patent No.: US 9,671,411 B2
(45) Date of Patent: *Jun. 6, 2017

(54) MONOCYTE ACTIVATION TEST BETTER ABLE TO DETECT NON-ENDOTOXIN PYROGENIC CONTAMINANTS IN MEDICAL PRODUCTS

(71) Applicants: BAXTER INTERNATIONAL INC., Deerfield, IL (US); BAXTER HEALTHCARE SA, Glattpark (CH); THE SECRETARY OF STATE FOR HEALTH, London (GB)

(72) Inventors: Stephen Poole, London (GB); Mehul Patel, Malvern, PA (US)

(73) Assignees: BAXTER INTERNATIONAL INC., Deerfield, IL (US); BAXTER HEALTHCARE SA, Glattpark (Opfikon) (CH); THE SECRETARY OF STATE FOR HEALTH, London (GB)

( * ) Notice: Subject to any disclaimer, the term of this patent is extended or adjusted under 35 U.S.C. 154(b) by 4 days.

This patent is subject to a terminal disclaimer.

(21) Appl. No.: 14/679,651

(22) Filed: Apr. 6, 2015

(65) Prior Publication Data
US 2015/0285819 A1  Oct. 8, 2015

Related U.S. Application Data

(60) Continuation of application No. 13/293,868, filed on Nov. 10, 2011, now Pat. No. 9,023,647, which is a continuation of application No. 12/767,514, filed on Apr. 26, 2010, now Pat. No. 8,058,021, which is a division of application No. 11/613,866, filed on Dec. 20, 2006, now Pat. No. 7,736,863.

(60) Provisional application No. 60/752,970, filed on Dec. 22, 2005.

(51) Int. Cl.
G01N 33/00 (2006.01)
G01N 33/68 (2006.01)
G01N 33/50 (2006.01)

(52) U.S. Cl.
CPC ..... *G01N 33/6869* (2013.01); *G01N 33/5047* (2013.01); *G01N 33/5055* (2013.01); *G01N 33/5091* (2013.01); *G01N 33/6863* (2013.01); *G01N 2333/5412* (2013.01); *G01N 2800/7095* (2013.01)

(58) Field of Classification Search
CPC ........... G01N 33/5055; G01N 33/5091; G01N 33/6898; G01N 33/6863; G01N 33/5047
See application file for complete search history.

(56) References Cited

U.S. PATENT DOCUMENTS

| 4,434,237 | A | 2/1984 | Dinarello |
| 5,128,270 | A | 7/1992 | Delacroix et al. |
| 5,281,540 | A | 1/1994 | Merkh et al. |
| 5,891,728 | A | 4/1999 | Wendel et al. |
| 6,696,261 | B2 | 2/2004 | Patel et al. |
| 7,736,863 | B2 * | 6/2010 | Poole ................. G01N 33/5047 435/287.2 |
| 8,053,200 | B2 * | 11/2011 | Poole ................. G01N 33/5047 435/287.2 |
| 8,058,021 | B2 | 11/2011 | Poole et al. |
| 2001/0034037 | A1 | 10/2001 | Patel et al. |

FOREIGN PATENT DOCUMENTS

| WO | WO-93/02361 A1 | 2/1993 |
| WO | WO-94/10571 A1 | 5/1994 |
| WO | WO-95/18148 A1 | 7/1995 |
| WO | WO-01/48481 A1 | 7/2001 |

OTHER PUBLICATIONS

Carlin et al., In vitro pyrogenicity of a multivalent vaccine, Infanrix, *Pharmeuropa*, 15(3): 418-23 (2003).
Charles River Laboratories, Endosafe Times, 2(1): 1-6 (Sep. 2004).
Cruse et al., Illustrated Dictionary of Immunology, CRC Press, Inc., pp. 83, 248 (1995).
Cytotrap-IL-6 DIA Cytokine stimulation assay, protocol for an incubation of 24 hours (Aug. 5, 1999).
De Groote et al., Direct stimulation of cytokines (IL-1β, TNF-α, IL-6, IL-2, IFN-γ and GM-CSF) in whole blood. I. Comparison with isolated PBMC stimulation, *Cytokine*, 4(3): 239-48 (1992).
DeLay Ed. *Cytokine Protocols*, Humana Press, Totowa, NJ., pp. 47 and 207 (2004).
Desch et al., Production of human tumor necrosis factor from whole blood ex vivo, *Lymphokine Res.* 8(2): 141-6 (1989).
Dinarello et al., Human leukocytic pyrogen test for detection of pyrogenic material in growth hormone produced by recombinant *Escherichia coli*, *J. Clin. Microbiol.* 20(3):323-9 (1984).
Duff et al., The detection of endotoxin by in vitro production of endogenous pyrogen: Comparison with Limulus amebocyte lysate gelation, *J. Immunol. Meth.* 52: 323-31 (1982).
DynaMiX-TNF-D-DIA, Cytokin stimulation assay protocol for an incubation of 3 hours (May 7, 1997).
EDTNA/ERCA Guidelines: Technical Section, EDTNA/ERCA J. 28(3): 107-15 (2002).

(Continued)

Primary Examiner — Cherie M Stanfield
(74) Attorney, Agent, or Firm — Marshall, Gerstein & Borun LLP

(57) ABSTRACT

An improved monocyte activation test is described that is better able to detect non-endotoxin pyrogens in medical products, in which a sample is incubated with a monocyte-containing reagent in an assay system comprising at least one surface comprising polypropylene. The invention also concerns assay systems for use in these tests that include at least one microtiter well having at least one interior surface comprising polypropylene and having a shape such that monocyte-containing reagent is concentrated in the well to provide greater cell to cell contact. The invention also relates to a diagnostic kit that can be used to test for the presence of non-endotoxin pyrogens in a sample.

24 Claims, 16 Drawing Sheets

(56) References Cited

OTHER PUBLICATIONS

Emancipator et al., In vitro inactivation of bacterial endotoxin by human lipoproteins and apolipoproteins, *Infect. Immun.* 60: 596-601 (1992).
Eperon et al., Human monocytoid cell lines as indicators of endotoxin: comparison with rabbit pyrogen and Limulus amoebocyte lysate assay, *J. Immunol. Meth.* 207: 135-45 (1997).
Eperon et al., The use of human monocytoid lines as indicators of endotoxin, *J. Immunol. Meth.* 194: 121-9 (1996).
Fennrich et al., Detection of endotoxins and other pyrogens using human whole blood, *Dev. Biol Stand.* 101: 131-9 (1999).
Fennrich et al., New applications of the human whole blood pyrogen assay (PyroCheck), *ALTEX*, 16: 146-9 (1999).
Finch-Arietta et al., Cytokine production in whole blood ex vivo, *Agents Actions*, 34: ½ (1991).
Fujiwara et al., Measurement of endotoxin in blood products using an endotoxin-specific Limulus test reagent and its relation to pyrogenic activities in rabbit, *Yakugaku Zasshi*, 110 (5): 332-40 (1990).
Gaines-Das et al., Monocyte activation test for pro-inflammatory and pyrogenic contaminants of parenteral drugs: test design and data analysis, *J. Immunol. Meth.* 288(1-2): 165-77 (2004).
Hansen et al., Comparison of cultured human mononuclear cells, limulus amebocyte lysate and rabbits in the detection of pyrogens, *J. Clin. Pharm. Thera.* 15: 425-33 (1990).
Harlan Sera-Lab, 2004 Catalogue, cover page, index page, and pp. 1 and 24 (2004).
Harris et al., Detection of endotoxin in triglyceride-rich lipoproteins in vitro, *J. Laboratory Clin. Med.* 118: 186-93 (1991).
Hartung et al., Detection of pyrogens using human whole blood, *In Vitro Toxicology*, 9(4): 353-9 (1996).
Hartung et al., Novel pyrogen tests based on the human fever reaction, *Altern Lab Anim.* 29: 99-123 (2001).
Hoffmann et al., International validation of novel pyrogen tests based on human monocytoid cells, *J. Immunol. Meth.* 298: 161-73 (2005).
web.archive.org/web/2003101901343/nuncbrand.com/page.asp?ID =298⟨ = GB (NuncBrand FAQ for Immunology Products, published on the Internet at least since Jan. 2, 2004) (hereinafter "NuncBrand. com archive"), 7 pages.
Jahnke et al., Comparative testing for pyrogens in parenteral drugs using the human whole blood pyrogen test, the rabbit in vivo pyrogen test and the LAL test, *Eur. J. Parent. Sci.* 5(2): 39-44 (2000).
Martis et al., Aseptic peritonitis due to peptidoglycan contamination of pharmacopoeia standard dialysis solution, *Lancet*, 365: 588-94 (2005).
Mascoli et al., Applications and advantages of the limulus amebocyte lysate (LAL) pyrogen test for parenteral injectable products, *Prog. Clin. Biol. Res.* 29, pp. 387-402 (2003).
Mascoli et al., Limulus amebocyte lysate (LAL) test for detecting pyrogens in parenteral injectable products and medical devices: advantages to manufacturers and regulatory officials, *J. Parenter Drug Assoc.* 33(2): 81-95 (1979).
Medgenix update, TNF D and multiple sclerosis (May 1995).
Moesby et al., A comparative study of Mono Mac 6 cells, isolated mononuclear cells and Limulus amoebocyte lysate assay in pyrogen testing, *Internl. J. Pharmaceut.* 191: 141-9 (1999).
Moesby et al., Ultrasonication of pyrogenic microorganisms improves the detection of pyrogens in the Mono Mac 6 assay, *Eur. J. Pharmaceut. Sci.* 11: 51-7 (2000).
Moltz, Fever: Causes and consequences, *Neurosci. Biobeha y. Rev.* 17: 237-69 (1993).
Nakagawa, Evaluation of the in vitro pyrogen test system based on proinflammatory cytokine release form human monocytes: Comparison with a human whole blood culture test system and with the rabbit pyrogen test, *Clin. Diag. Lab. Immunol.* 9(3): 588-97 (2002).
Nerad et al., Interleukin-1p (IL-113), IL-1 receptor antagonist, and INFa production in whole blood, *J. Leuk. Biol.* 52: 687-92 (1992).
Peterbauer et al., Interferon-y-primed monocytoid cell lines: optimizing their use for in vitro detection of bacterial pyrogens, *J. Immunol. Meth.* 8488 (1999).
Peterbauer et al., Neopterin and nitrite in supernatants from interferon-y-treated monocytoid cell lines: A tool to identify bacterial pyrogens, *Pteridines*, 10: 112-8 (1999).
Pool et al., The detection of pyrogens in blood products using an ex vivo whole blood culture assay, *J. Immunoassay*, 19(2&3): 95-111 (1998).
Poole et al. A rapid 'one-plate' in vitro test for pyrogens, *J. Immunol. Meth.* 274(1-2): 209-20 (2003).
Poole et al., Towards a 'human pyrogen test', *Eur. J. Parent. Sci.* 6(2): 63-4 (2001).
Read et al., The protective effect of serum lipoproteins against bacterial lipopolysaccharide, *Eur. Heart J.* 14: 125-9 (1993).
Rose et al., Eds., Manual of Clinical Laboratory Immunology, Sixth Edition. ASM Press. Washington, DC. pp. 323 and 326 (2002).
Roslansky et al., Sensitivity of limulus amebocyte lysate (LAL) to LAL-reactive glucans, *J. Clin. Microbiol.* 29(11): 2477-83 (1991).
Rothwell, CNS regulation of thermogenesis, *Crit. Rev. Neurobiol.* 8(1/2): 1-10 (1994).
Taktak et al., Assay of pyrogens by interleukin-6 release from monocytic cell lines, *J. Pharm. Pharmacol.* 43: 578-82 (1991).
Tilders et al., Activation of the hypothalamus-pituitary-adrenal axis by bacterial endotoxins: routes and intermediate signals, *Psychoneuroendocrinology*, 19(2): 209-32 (1994).
Tsuchiya et al., Establishment and characterization of a human acute monocytic leukemia cell line (THP-1), *Int. J. Cancer*, 26: 171-6 (1980).
Yamamoto et al., A cell line assay system for predicting the response of human blood to endotoxin, *Jpn. J. Infect. Dis.* 56 (3): 93-100 (2003).
Zeisberger et al., Neurobiological concepts of fever generation and suppression, *Neuropsychobiology*, 28: 106-9 (1993).
Ziegler-Heitbrock et al., Establishment of a human cell line (Mono Mac 6) with characteristics of mature monocytes, *Int. J. Cancer*, 41: 456-61 (1988).
Pulsoni et al., Cell to cell contact enhances the proliferation of acute myeloid leukemia (AML) cells in vitro without an apparent role of adhesion glycoproteins LFA1, MAC1, and P150-95, *Leuk. Res.* 13(10): 883-91 (1989).

\* cited by examiner

MONOCYTE ACTIVATION TEST BETTER ABLE TO DETECT NON-ENDOTOXIN PYROGENIC CONTAMINANTS IN MEDICAL PRODUCTS

FIELD OF INVENTION

The present invention generally concerns an improved monocyte activation test that is better able to detect non-endotoxin pyrogens in medical products, in which a sample is incubated with a monocyte-containing reagent in an assay system comprising at least one surface comprising polypropylene. The invention also concerns assay systems for use in these tests that include at least one microtiter well having at least one interior surface comprising polypropylene and having a shape such that monocyte-containing reagent is concentrated in the well to provide greater cell to cell contact. The invention also relates to a diagnostic kit that can be used to test for the presence of non-endotoxin pyrogens in a sample.

BACKGROUND OF THE INVENTION

When certain chemical or biological compounds are brought into contact with the circulatory system of humans or other mammals, they cause a systemic response known as the inflammatory response or inflammation. The inflammatory response is a defense mechanism to protect the body from infection and/or injury; inflammation increases blood flow to the site of infection or injury, bringing necessary fluids, proteins, and white blood cells (leukocytes) to help in the healing process. For example, one symptom associated with the inflammatory response is an elevation in body temperature or fever, which functions as a defense mechanism to pathogens that cause overheating. The inflammatory response may be associated with a variety of "flu-like" symptoms including fever, chills, fatigue, headaches, loss of appetite, and muscle stiffness. A chemical or biological compound that triggers fever has historically been referred to as a "pyrogen" or a "pyrogenic" compound, referring to the fever response which such compounds may cause. Some chemical or biological compounds, however, are generally pro-inflammatory and may or may not cause fever as part of the inflammatory response that they cause.

In some cases, depending on the sensitivity of an individual and the type and concentration of pyrogen the individual is exposed to, an individual can develop life-threatening shock-like symptoms after exposure to a pyrogen. Medical products which can be inhaled, injected, or infused and medical devices such as membranes or implanted materials pose a particular risk of pyrogenicity. Even nutrients can represent a risk of pyrogenicity. Pyrogens contained in medical products and nutrients are referred to as exogenous pyrogens; in contrast, endogenous pyrogens are messenger compounds of the immune system that mediate an individual's inflammatory response to exogenous pyrogens. In addition to the pyrogenic nature of a product itself or by-products of its production, contamination of the product can often cause pyrogenicity. Pyrogenicity due to contamination of a product can be caused by any one of a diverse group of pyrogens derived from bacteria, viruses, fungi, or even from the host. This problem can persist even if the product is "sterilized" by heat or chemical methods; a commonly encountered pyrogenic compound, bacterial endotoxin (consisting largely of lipopolysaccharide (LPS) from the cell wall of Gram-negative bacteria), can remain after the bacteria are killed. Thus, pyrogen testing of various pharmaceuticals, nutrients, and medical products for parenteral application is necessary in order to ensure the safety of such products.

Usually, compounds which act as a pyrogen do so by stimulating the production of endogenous pyrogens, such as prostaglandins and proinflammatory cytokines, in monocytes after contact with tissue, cells, or body fluids. It is these endogenously produced pyrogens which mediate the inflammatory response in the affected organism. The most important and well-known of these endogenous pyrogens are the cytokines interleukin-1 (IL-1), interleukin-6 (IL-6), interleukin-8 (IL-8) and tumor necrosis factor (TNF) and the low molecular weight lipid mediator prostaglandin E2 ($PGE_2$). These compounds are routinely assayed by ELISA, or enzyme-linked immunosorbent assays (for IL-1, IL-6, or TNF), and EIA, or enzyme immunoassay (for $PGE_2$).

In order to avoid a pyrogenic reaction and ensure the safety of any drug or pharmaceutical product administered parenterally, pyrogenic contamination must be monitored to identify individual lots that are contaminated with bacterial contaminants. Two animal-based Pharmacopial methods, the Limulus amebocyte lysate (LAL) test, also referred to as the bacterial endotoxins test (BET), and the rabbit pyrogen test, are currently routinely used to monitor pyrogen contamination in mass-produced pharmaceutical products.

The rabbit test is an in-vivo test which consists of injecting a statistically significant number of rabbits with the sample compound and observing the average rise in body temperature elicited in the test animals. Although the rabbit test is responsive to a wide spectrum of pyrogenic agents, including non-endotoxin pyrogens, the rabbit test has a relatively low sensitivity (ng endotoxin/ml) compared to other pyrogen tests (pg endotoxin/ml for the LAL test). In addition, the correlation of pyrogenic responses to compounds between species is, at best, approximate. It has been documented, for instance, that the dose of bacterial endotoxin eliciting a pyrogenic response varies as much as 10,000 fold between species. The relative insensitivity, poor quantitative results, variability between rabbit species, and ethical issues involved in animal testing have made the rabbit test disfavored in recent years.

In contrast to the rabbit test, which detects a wide range of pyrogens, the LAL test only detects endotoxin pyrogens. Bacterial endotoxin, e.g., lipopolysaccharide (LPS), which comes from the cell wall of Gram-negative bacteria, is one of the best described pyrogenic compounds (Moltz et al., *Neurosci. Biobehav. Rev.,* 1993, 17, 237-269; Tilders et al., *Psychoneuroendocrinology,* 1994, 19, 209-232; Rothwell, *Crit. Rev. Neurobiol.,* 1994, 8, 1-10; Zeisberger and Roth, *Neuropsychobioloqy,* 1993, 28, 106-109). It was therefore thought to be generally useful to replace expensive and time consuming rabbit experiments with a direct LAL test for bacterial endotoxin. This approach has obvious limitations. The LAL test is a very sensitive in-vitro test; however, it only detects endotoxins from Gram-negative bacteria and gives false negative results with certain products which can still stimulate monocytes to make pyrogenic cytokines. The LAL test is also susceptible to interference by, for example, high protein levels of test substances or by glucans (Roslansky and Novitsky, *J. Clin. Microbiol.,* 1991, 29, 2477; Fennrich et al., *Dev. Biol. Stand.,* 1999, 101, 131). On the other hand, the Limulus test is so sensitive that it is easily prone to false positive results due to impurities that are not relevant to product quality (Fujiwara et al., *Yakuqaku Zasshi,* 1990, 110, 332-340).

Thus, a need existed for a non-animal-based test system that is characterized by high sensitivity, high specificity, and the ability to detect a wide range of pyrogens. With this intent and with an improved understanding of the human inflammatory response, test systems based on the in vitro activation of human monocytes were developed. Some 20 years ago, researchers used peripheral blood mononuclear cells (PBMC) to detect endotoxin by monitoring the release of pyrogenic cytokines. (Dinarello et al., *J. Clin. Microbiol.,* 1984, 20, 323; Duff and Atkins, *J. Immunol. Methods,* 1982, 52, 323). Since then, several different test systems using different sources of human monocytes, including human peripheral whole blood (WB), PBMCs, or monocytic cell lines, such as MONOMAC-6 (MM6) (Ziegler-Heitbrock et al., Int. J. Cancer, 1988, 41, 456) or THP-1 (Tsuchiya et al., *Int. J. Cancer,* 1980, 26, 171), and various readouts, including the pyrogenic cytokines tumor necrosis factor alpha, TNF-α, IL-6, IL-1β, and the non-pyrogenic metabolite neopterin (Hartung et al., The Report and Recommendations of ECVAM Workshop 43, 2001, 29, 99; Poole and Gaines Das, *Eur J Parenteral Sciences,* 2001, 6, 63; Poole et al., *J. Immunol. Methods,* 2003, 274, 209; Gaines Das et al., *J Immunol Methods,* 2004, 288, 165), have been developed. Recently, in a collaborative European study, the Human(e) Study, six of the most prominent monocyte activation tests, each using a different combination of the above described cell sources and readouts were evaluated for the ability to detect endotoxin in medical products spiked with various concentrations of pure endotoxin.

In five of the six tests, the cells were cultured on 96-well polystyrene plates with flat bottomed wells (Hoffmann et al., *J. Immunol. Methods,* 2005, 298, 161). In the sixth test (based on Fennrich et al., *Dev. Biol. Stand.,* 1999; Fennrich et al., *ALTEX,* 1999; Hartung et al., 2001), Eppendorf centrifuge tubes (1.2 ml) made of polystyrene, with conical bottoms, were used for the greater part of the evaluation and, part way into the study, polypropylene tubes (1.5 ml), with round bottoms, were substituted for the polyethylene tubes by Charles River Laboratories, the manufacturer of the Endosafe® In vitro Pyrogen Test (IPT) kit used in the study. This substitution was not reported to have any significant effect on the test, and the polypropylene tubes themselves were thereafter replaced with flat-bottomed polystyrene 96-well plates, when Charles River Laboratories modified the Endosafe® IPT for reduced volumes. The source of monocytes in this test was whole blood and the readout was IL-1β. Whole blood was incubated with various drugs spiked with different concentrations of endotoxin.

Carlin and Viitanen disclose a monocyte activation test, based on whole blood or MONOMAC-6 cells as the source of monocytes and IL-6 as the readout, for evaluating the inherent pyrogenicity of the vaccine Infanrix, which contains Gram-positive and Gram-negative antigens, including various non-endotoxin pyrogens, i.e., Diphtheria toxoid, Pertussis toxoid, and Tetanus toxoid (*Pharmeuropa,* 2003, 15, 3, 418-423). Cells were cultured at low cell density in endotoxin-free Eppendorf Bio-Pure grade tubes of undisclosed composition. The pyrogenicity of the vaccine was not the result of contamination of the vaccine during its manufacture or storage. Hartung and Wendel disclose a monocyte activation test, based on whole blood as the source of monocytes and IL-1β as the preferred readout, for detecting endotoxin and non-endotoxin pyrogens in their pure forms, i.e., LPS from *Salmonella abortus* equi, streptolysin O (SLO) from *Streptococcus* pyrogens, and muramyl dipeptide (MDP) (Hartung and Wendel, *In Vitro Toxicology,* 1996, 9, 4, 353-359; U.S. Pat. No. 5,891,728). Cells were cultured in polypropylene tubes.

Yamamoto et al. disclose a monocyte activation test, based on whole blood or cells from different human cell lines, the 28SC cell line being preferred, as the source of monocytes/monocytic cells and IL-6 as the preferred readout, for detecting endotoxin pyrogens (*Jpn. J. Infect. Dis.,* 2003, 56, 93-100). The endotoxin test is said to predict the possibility of an in vivo synergism between endotoxin and a parenteral drug, particularly interferon, such that the drug augments the pyrogenic effects of the endotoxin. Cells were cultured with either endotoxin in its pure form or a mixture of endotoxin in its pure form and human interferon. Cell line cells were cultured in polystyrene 96-well plates with flat-bottomed wells. Blood cells were cultured in tubes of unspecified material.

Nakagawa et al. describe a monocyte activation test, based on whole blood or MM6-CA8 cells (a subclone of MONOMAC-6) as the source of monocytes and IL-6 as the preferred readout, for detecting endotoxin and non-endotoxin pyrogens in their pure forms, i.e., LPS from *E. coli* O55:B5 and insoluble peptidoglycan (PG) derived from *S. aureus* (*Clinical and Diagnostic Laboratory Immunol.,* 2002, 9, 3, 588-597). MM6-CA8 cells were cultured in polystyrene 96-well plates. Blood cells were cultured in polypropylene tubes; the volumes used (225 µL of blood, 25 µL of test solution, 750 µL of saline) precluded the used of standard 96-well plates (250 µL/well).

Recently, various sources indicate that polypropylene is to be avoided in pyrogen testing. For example, Charles River Laboratories recommends avoiding polypropylene because the hydrophobic nature of a polypropylene surface could result in the adsorption of endotoxin on such a surface due to the hydrophobic domains associated with the Lipid A component of LPS (Charles River Laboratories, *Endosafe Times,* September 2004). Harlan Sera-Lab, a manufacturer of biosafety tests, states that polypropylene tubes can interfere with the LAL assay (Harlan Sera-Lab, 2004 Catalogue). And, the European Dialysis and Transplant Nurses Association as well as the European Renal Care Association recommend avoiding polypropylene and using polystyrene in endotoxin testing because polystyrene does not normally adsorb endotoxin (EDTNA/ERCA Guidelines).

Thus, a need exists for a non-animal-based pyrogen test, characterized by high sensitivity, high specificity, and the ability to detect a wide range of pyrogenic contaminants in medical products.

SUMMARY OF THE INVENTION

Applicants have developed an in-vitro pyrogen test that is sensitive and detects pyrogenic contaminants present in medical products. Generally, the present invention is directed to a method of detecting non-endotoxin pyrogens in a sample by combining monocytes, i.e., in the form of a monocyte-containing reagent, and the sample to be tested in a first assay system comprising at least one surface comprising polypropylene, such that the monocytes are in contact with the surface. The monocytes and the sample are incubated so that the monocytes produce a cytokine or an endogenous mediator of the inflammatory response during incubation. The contents of the first assay system are transferred to a second assay system comprising at least one surface treated with an antibody to a cytokine or an endogenous mediator or marker of the inflammatory response. The second assay system is assayed for the presence of cytokine or endogenous mediator bound to the antibody on the surface. When the monocytes used in this method are PBMCs or monocytic cell line cells, the monocytes are present in the assay systems at a high cell density.

The present invention is also generally directed to a method of detecting non-endotoxin pyrogens in a parenterally-administered medical product by combining whole blood, as the monocyte-containing reagent, and the medical product to be tested in a first assay system comprising at least one surface comprising polypropylene, such that the blood is in contact with the surface. The blood and the medical product are incubated such that the blood produces the cytokine IL-6 during incubation. The contents of the first assay system are transferred to a second assay system comprising at least one surface treated with an antibody to IL-6. The second assay system is assayed for the presence of IL-6 bound to the antibody on the surface.

The present invention is further drawn to a method of culturing monocytes, i.e., in the form of a monocyte-containing reagent, for use in a non-endotoxin pyrogen test by combining the monocytes and a sample to be tested in an assay system comprising at least one surface comprising polypropylene, such that the monocytes are in contact with the surface.

The invention is also drawn to a method of culturing monocytes as part of a non-endotoxin pyrogen test by combining the monocytes and a sample in an assay system comprising at least one microtiter well shaped such that the monocyte-containing reagent is concentrated as compared to a flat-bottomed microtiter well, a surface of the well comprising polypropylene, such that the monocytes are in contact with the surface. When the monocytes used in these culturing methods are peripheral blood mononuclear cells (PBMC) or monocytic cell line cells, the monocytes are present in the assay systems at a high cell density.

The invention is also directed to a method of detecting non-endotoxin pyrogens in a parenterally administered medical product by combining whole blood, as the monocyte-containing reagent, and the medical product to be tested in an assay system comprising at least one surface comprising polypropylene and at least one surface treated with an antibody to IL-6, such that the blood is in contact with the surface comprising polypropylene, and assaying the assay system for the presence of IL-6 bound to the antibody on the surface.

The invention further provides a diagnostic kit which contains a microtiter plate comprising a plurality of microtiter wells shaped such that culture medium contained in each well is concentrated as compared to a flat-bottomed microtiter well, a surface of each well comprising polypropylene, and cryopreserved monocytes, i.e., in the form of a cryopreserved monocyte-containing reagent, contained in the wells of the microtiter plate, such that the monocytes are in contact with the surfaces of the wells. When the monocytes in the kit are peripheral blood mononuclear cells (PBMC) or monocytic cell line cells, the monocytes are present in the wells at a high cell density.

The invention also provides a diagnostic kit which contains an assay system for detecting non-endotoxin pyrogens in a parenterally administered medical product, the assay system comprising a microtiter plate comprising a plurality of microtiter wells shaped such that culture medium contained in each well is concentrated as compared to a flat-bottomed microtiter well, a surface of each well comprising polypropylene, cryopreserved whole blood, as the cryopreserved monocyte-containing reagent, contained in the wells of the microtiter plate, such that the blood is in contact with the surfaces of the wells, and an antibody to IL-6.

Other objects and features of this invention will be in part apparent and in part pointed out hereinafter.

DETAILED DESCRIPTION OF THE INVENTION

Figure 1:
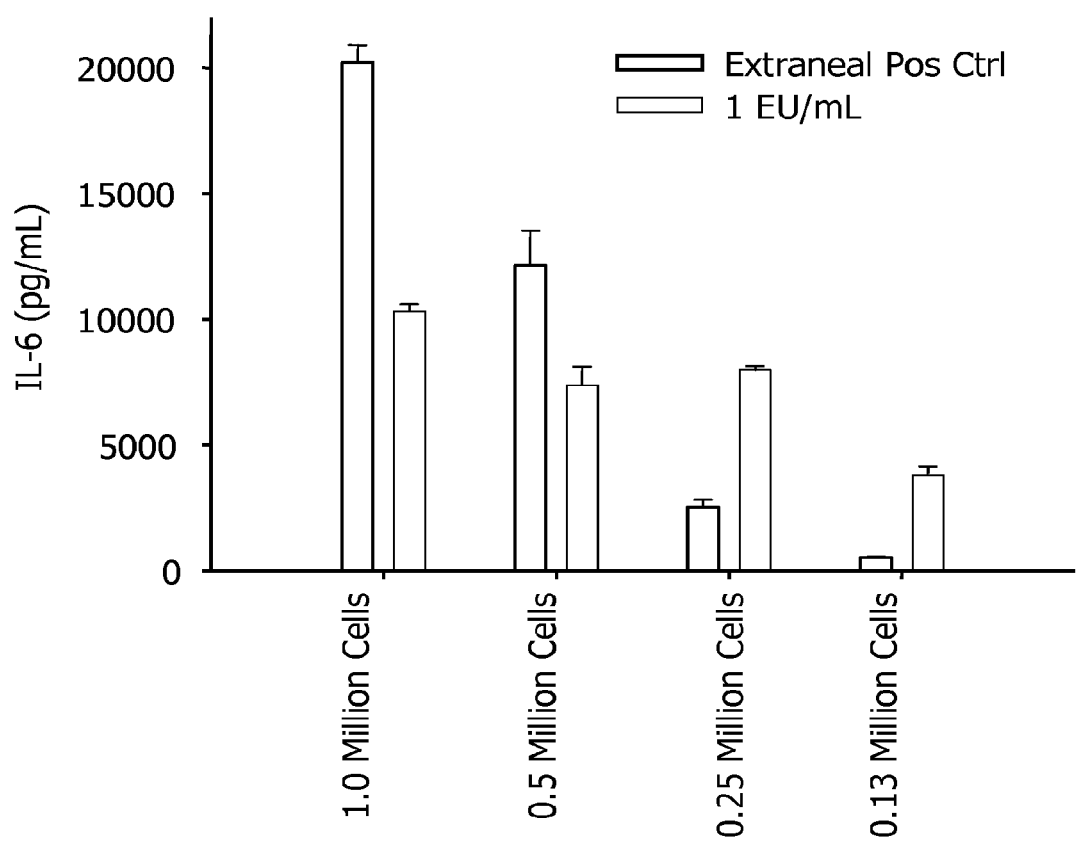
FIG. 1 is a graph depicting IL-6 responses for test samples having four different cell densities (1 million, 0.5 million, 0.25 million and 0.13 million PBMC per 250 µl well) in a monocyte activation test carried out with peripheral blood mononuclear cells on polypropylene plates with round-bottomed wells, with IL-6 as the readout. IL-6 responses are to endotoxin standard (1 endotoxin unit per ml) and Extraneal® positive control (i.e. a batch of this product contaminated with non-endotoxin pyrogen).
Figure 2:
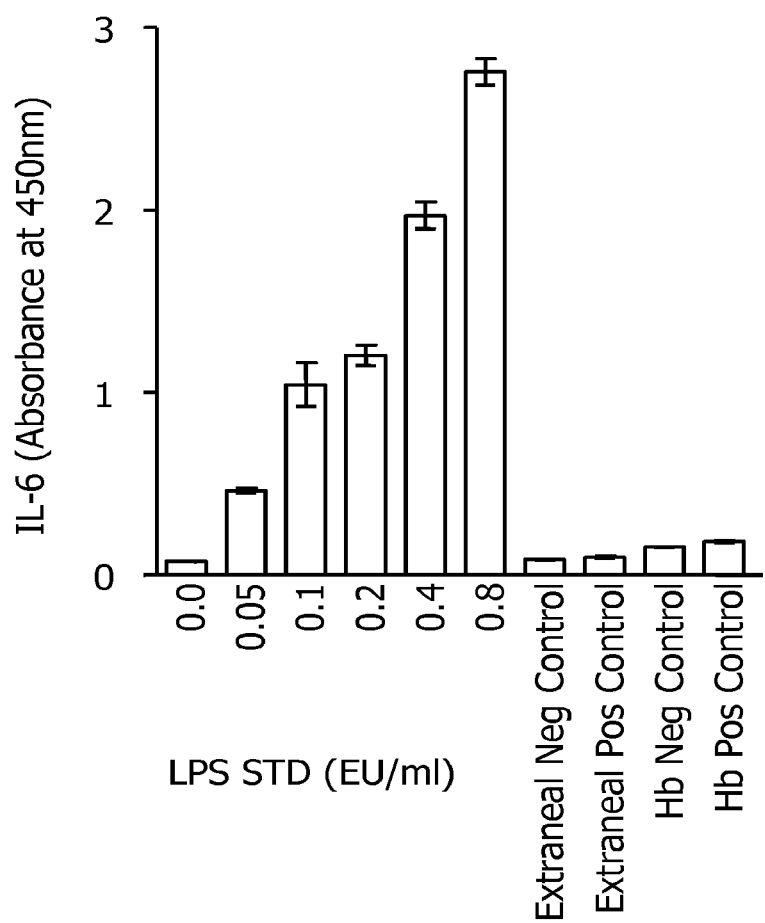
FIG. 2 is a graph illustrating IL-6 responses for test samples having low cell density in a monocyte activation test carried out with whole blood on polystyrene plates with flat-bottomed wells. IL-6 responses are to LPS, Extraneal® negative control (i.e. a clean batch of this product), Extraneal® positive control, Hemoglobin (Hb) negative control (i.e. a clean batch of this product), and Hemoglobin (Hb) positive control (i.e. a batch of this product contaminated with non-endotoxin pyrogen).
Figure 3:
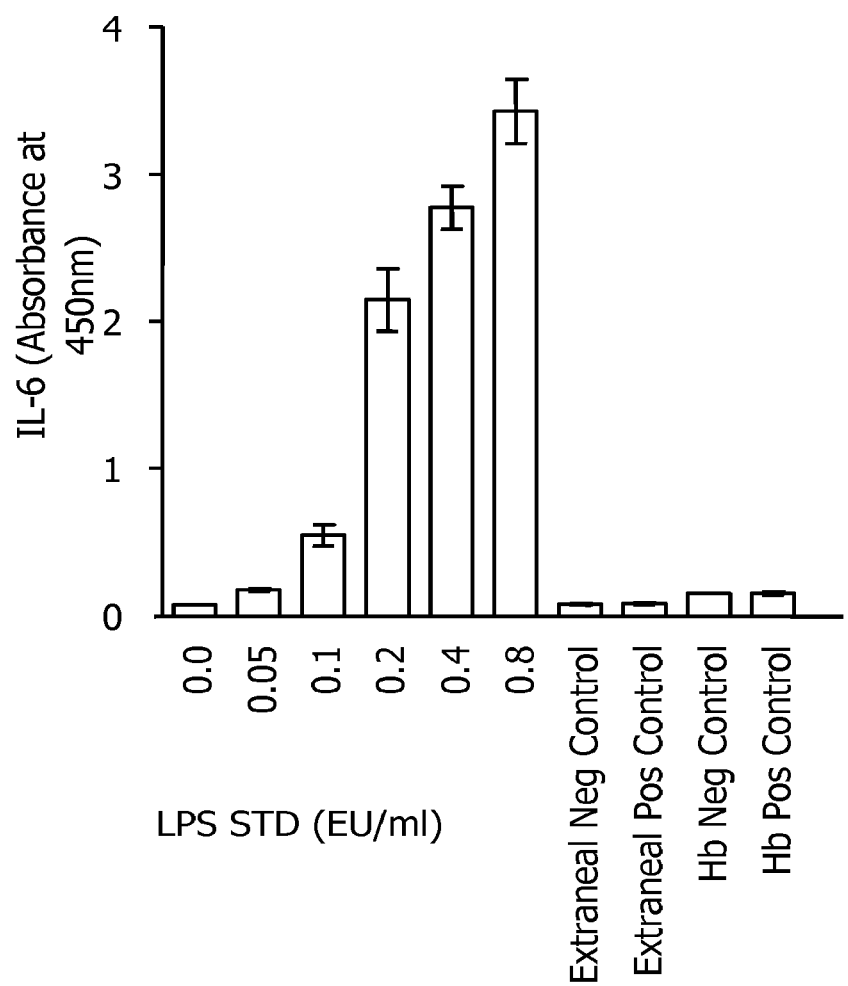
FIG. 3 is a graph illustrating IL-6 responses for test samples having low cell density in a monocyte activation test carried out with peripheral blood mononuclear cells on polystyrene plates with flat-bottomed wells. IL-6 responses are to LPS, Extraneal® positive and negative controls and Hb positive and negative controls.
Figure 4:
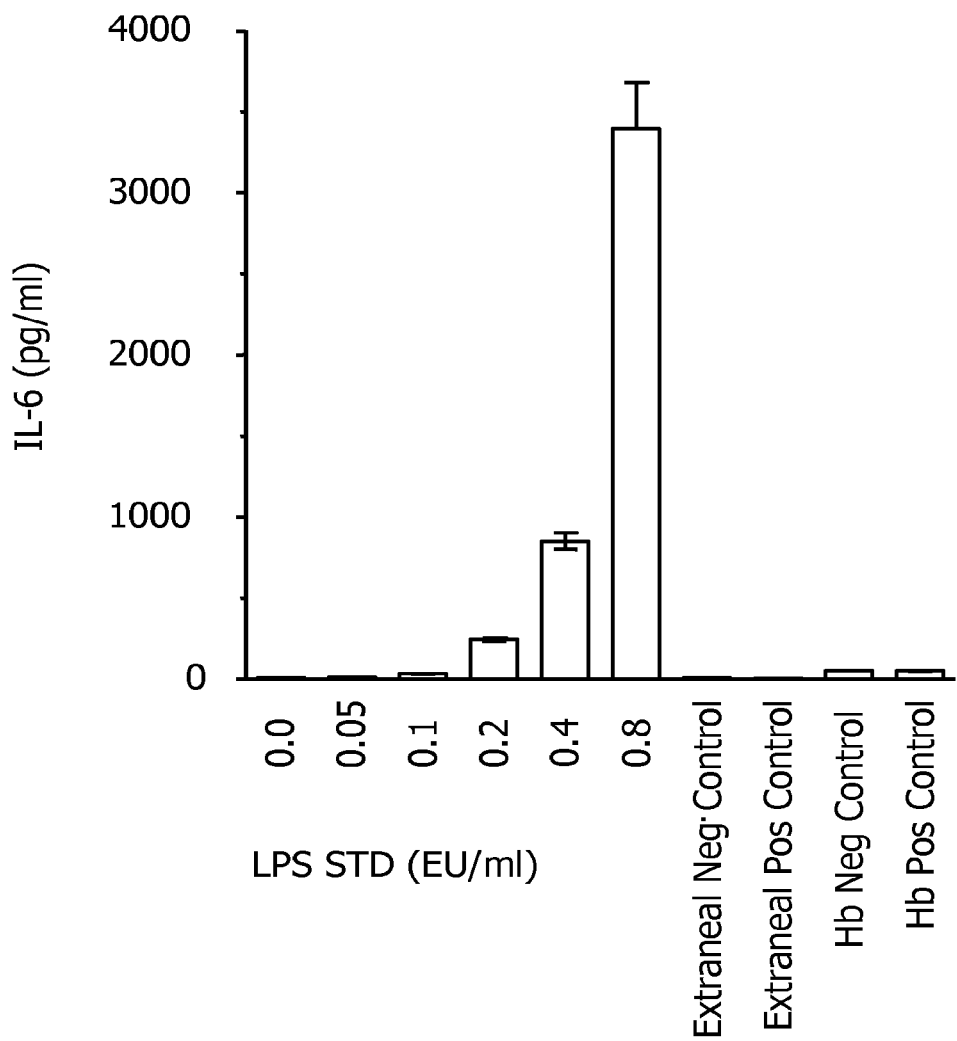
FIG. 4 is a graph illustrating IL-6 responses for test samples having low cell density in a monocyte activation test carried out with MONOMAC6 cells on polystyrene plates with flat-bottomed wells. IL-6 responses are to LPS, Extraneal® positive and negative controls and Hb positive and negative controls.
Figure 5:
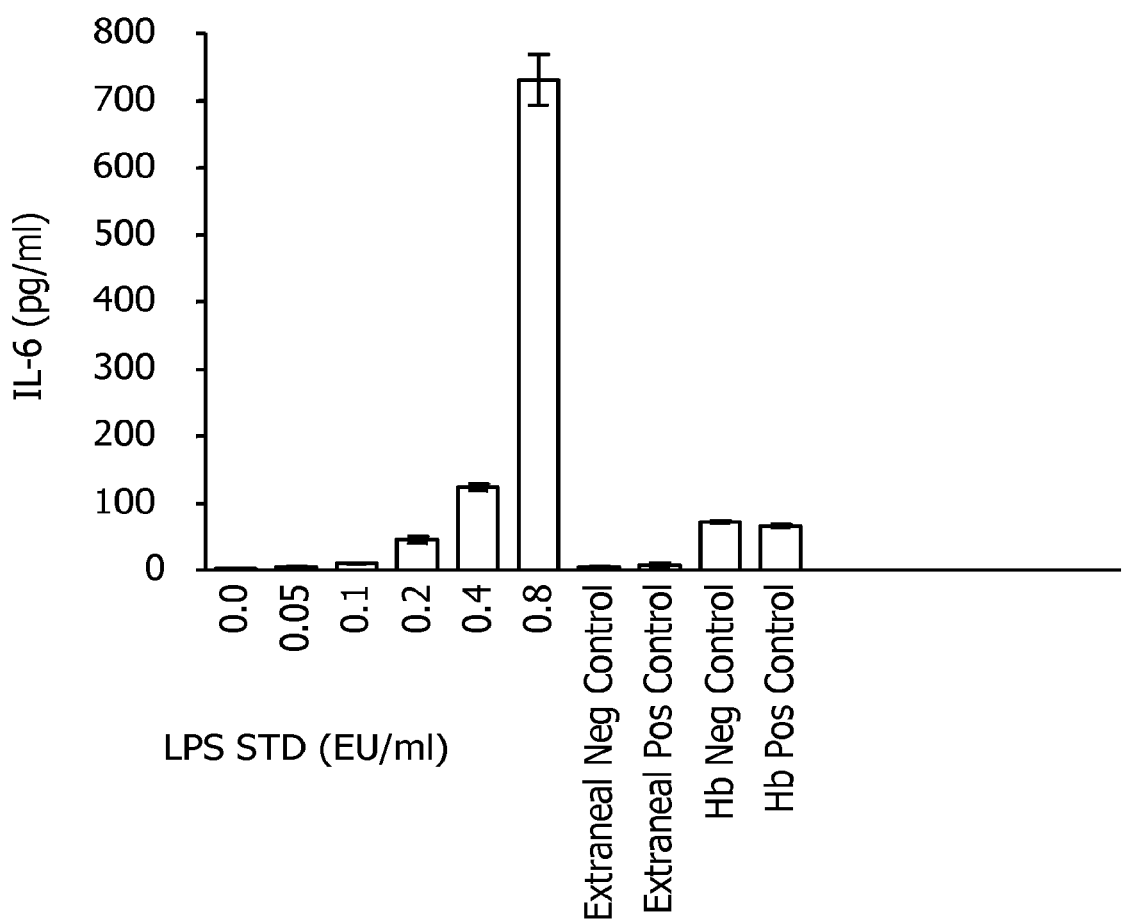
FIG. 5 is a graph depicting IL-6 responses for test samples having low cell density in a monocyte activation test carried out with THP-1 cells on polystyrene plates with flat-bottomed wells. IL-6 responses are to LPS, Extraneal® positive and negative controls and Hb positive and negative controls.

Pyrogens stimulate blood monocytes (as well as other leukocytes) and macrophages to produce and release numerous endogenous pyrogenic mediators of the inflammatory response, including cytokines (e.g. TNF-α, IL-1β, and IL-6). The release of these pyrogenic mediators into the circulation triggers a cascade of events leading to an inflammatory response in the affected individual. The monocyte activation test of the present invention relies on the measurement of these endogenous pyrogens as a marker for an inflammatory response. According to a preferred embodiment of the present invention, a sample is incubated with a monocyte-containing reagent in a first assay system comprising a surface comprised of polypropylene, the monocyte-containing reagent being present in the assay system at a high cell density. The contents of the first assay system are then transferred to a second assay system comprising a surface coated with anti-cytokine antibodies, and the second assay system is assayed for the presence of cytokines bound to the surface by the antibodies.

The pyrogen tests of the present invention are used to detect non-endotoxin pyrogens, i.e., Gram-positive bacteria (e.g., *Staphylococcus aureus*) or their components (e.g., muropeptide, lipoteichoic acid, enterotoxins, streptolysin), immune stimulators such as phytohemagglutimin or phorbolesteras, as well as endotoxin. Because the test utilizes the cytokine response of monocytes to diverse pyrogens rather than a response specific to Gram-negative bacterial endotoxin, a wide spectrum of pyrogenic agents can be detected with the test of the present invention.

The pyrogen tests of the present invention have been shown to be more effective in detecting non-endotoxin pyrogen in contaminated lots of a medical product as compared to conventional tests. The examples herein show that these conventional tests are incapable of distinguishing positive control samples of Extraneal® peritoneal dialysis solution, hemoglobin, or dextran from negative control samples of the same parenterals. The Extraneal® positive control sample was obtained from a product lot contaminated with non-endotoxin pyrogen; the contaminated lot caused adverse reactions in humans but tested negative for the presence of pyrogen according to an LAL test, which only tests for endotoxin pyrogens (Martis, et al., *Lancet*, 365(9459), 588). The hemoglobin positive control sample was also obtained from a product lot contaminated with non-endotoxin pyrogen; the contaminated lot caused fever responses in rabbits, but tested negative for the presence of pyrogen according to an LAL test. The dextran positive control was a preparation of dextran that had been found to cause fever in humans but tested negative for the presence of pyrogen according to an LAL test. The ability of the test to detect non-endotoxin contaminants in medical products is of great value as it enables identification of contaminated medical product lots before the lot is released for use in patients. Known tests function well in the context of detecting pure non-endotoxin and endotoxin pyrogen, i.e., peptidoglycan (PG) from *S. aureus* and LPS from *E. coli* as disclosed by Nakagawa et al. as discussed above, or the endotoxin spiking of products, i.e., various drugs were spiked with different concentrations of endotoxin in the six tests of the Human(e) Study as discussed above. LAL tests function effectively provided a medical product is contaminated with endotoxin (Mascoli, C. C., Weary, M. E., *J Parenter Drug Assoc.* 2003, 33, 81; Mascoli, C. C., Weary, M. E., *Prog Clin Biol Res.* 2003, 29, 387). However, when a medical product is contaminated with non-endotoxin pyrogen, such tests fail to detect the pyrogen. Without being bound to a particular theory, it is believed that the non-endotoxin pyrogen interacts with the medical product resulting in a "masking" of the pyrogen and the inability to detect non-endotoxin contaminants.

Figure 9:
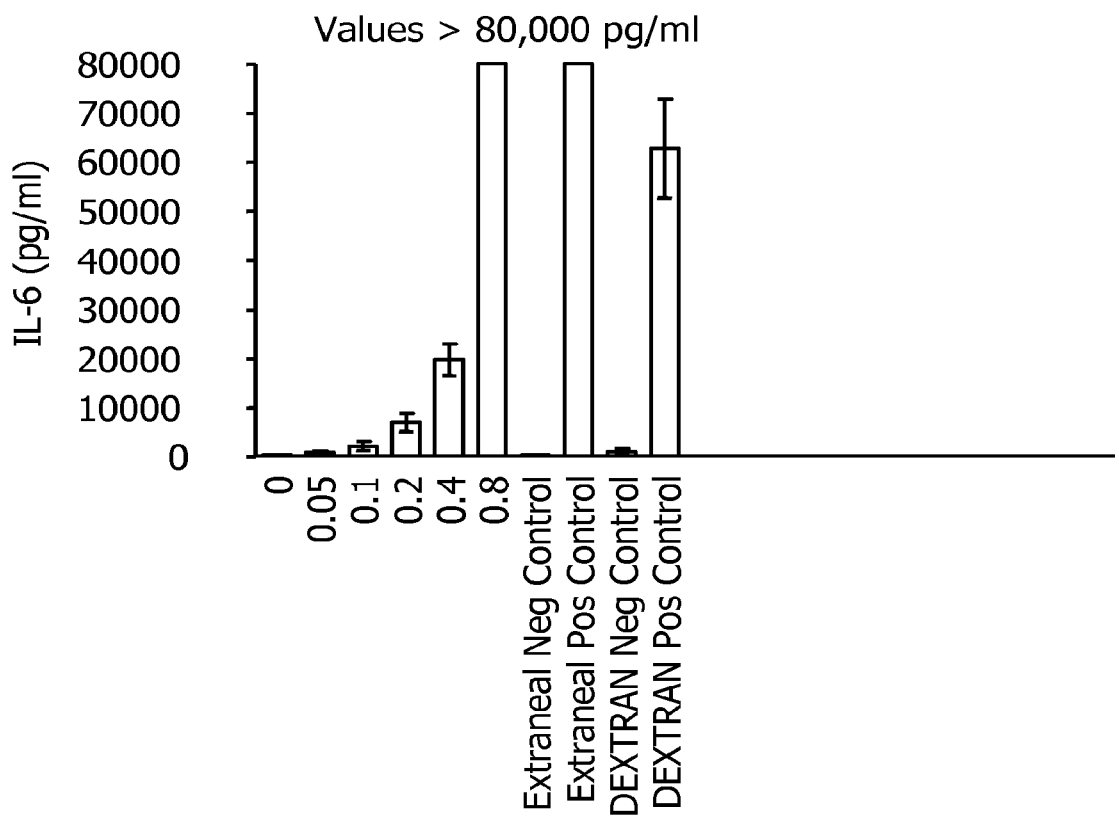
FIG. 9 is a graph depicting IL-6 responses for test samples having high cell density in a monocyte activation test carried out with peripheral blood mononuclear cells on polypropylene plates with round-bottomed wells. IL-6 responses are to LPS, Extraneal® positive and negative controls and dextran positive and negative controls.

The pyrogen tests of the present invention overcome this masking effect and are capable of detecting non-endotoxin contaminants in medical products: for example, in a preferred embodiment, in which PBMCs were cultured at a high cell density in round-bottomed polypropylene wells, the pyrogen test of the present invention was capable of distinguishing between positive and negative control samples of Extraneal® solution and dextran (see FIG. 9). None of the available kits that were tested were capable of distinguishing between positive and negative Extraneal® or hemoglobin controls (see FIGS. 1-8). Again, without being bound to a particular theory, it is believed that high cell densities provide more cells for greater cell to cell contact. Increased cell to cell contact facilitates greater communication between cells and, therefore, results in an enhanced inflammatory response to a pyrogenic contaminant. Cells communicate with each other via soluble mediators, such as cytokines, and via cell to cell contact, in which cytokines can also take part. A round-bottomed well, or a well generally shaped such that cells are concentrated, provides greater cell to cell contact as compared to a flat-bottomed well. And, it is believed that polypropylene increases the bioavailability of non-endotoxin pyrogens. Again, without being bound to a particular theory, it is believed that surface treatment of polystyrene plates as conventionally used in cell culture makes their surface less hydrophobic and better able to bind cells but also causes their surface to bind and neutralize non-endotoxin pyrogens. The polypropylene plate is not surface-treated so that it remains more hydrophobic than the polystyrene plate and less likely to neutralize non-endotoxin pyrogens.

1. Pyrogen Test Components

A pyrogen test which is characterized by some combination of the three elements described above, high cell density, round-bottom (or a different, appropriate shape), and polypropylene, i.e., PBMCs present at a high cell density in a round-bottomed polystyrene well, allows for improved detection of non-endotoxin contamination in medical products. The pyrogen tests of the present invention can be used to test a variety of medical products for the presence of non-endotoxin contamination, including blood products, medical products for parenteral administration, dialysates, vaccines, intravenous solutions, and any fluid that contacts the body or bodily fluids.

A. Cytokine or Endogenous Mediator of the Inflammatory Response

Any endogenous mediator of the inflammatory response secreted by the monocyte-containing reagent that is detectable may be used as the basis of the pyrogen test of the present invention. Preferably, however, a cytokine or endothelin marker is employed because they are easy to detect by the method of the invention. It has been found that monocytes in whole blood incubated with an endotoxin or non-endotoxin pyrogen produce several classes of cytokines, including, but not limited to pro-inflammatory cytokines (TNF-α, IL-1, IL-6), anti-inflammatory cytokines (IL-4, IL-10, IL-13, IL-1ra, TGF), Th1 (IL-2, IFN, IL-12), Th2 (IL-4, IL-5, IL-6, IL-10, IL-13), IL-1β, IL-1ra, IL-8, and PGE$_2$. Preferred cytokine markers for use in the invention include TNF-α, IL-1β, IL-1ra, IL-6, IL-8 and PGE$_2$. IL-6 is a particularly preferred cytokine marker to assay in the present invention. IL-6 is produced in detectable amounts within a relatively short incubation period. Immunoreactive IL-6, unlike immunoreactive IL-1β and TNFα, is secreted entirely into the cell-conditioned medium/blood, in large quantities, permitting its complete estimation. In contrast, immunoreactive TNFα and IL-1β remain largely intracellular, raising the possibility that test preparations affecting cell-permeability might more easily interfere in the test with (immunoreactive) TNFα or IL-1β as the readout, rather than IL-6 (see FIGS. 2 and 3). Nevertheless, TNF-α or IL-1β could also be used as a cytokine marker in the present invention. TNF-α is produced earlier than IL-6 in the monocyte pyrogen response. Thus, an embodiment of the invention which assays TNF-α would use a shorter incubation time (~1 to 2 hours) than embodiments which assay IL-6. Different pyrogenic contaminants may elicit different cytokine responses in the cell culture. Therefore, the invention may be tailored to detect the formation of particular cytokines when contamination with a particular pyrogen which causes secretion of those cytokines is probable for a pharmaceutical product.

B. Antibody to the Cytokine or Endogenous Mediator

Once the cytokine to be assayed has been determined, an antibody to that cytokine must be made for use in the present invention. Polyclonal antibodies purified under stringent conditions, as described in Example 1 of U.S. Pat. No. 6,696,261, which is incorporated herein by reference in its entirety, work well in the pyrogen test. Because the animal blood from which the polyclonal antibodies are isolated is naturally pyrogen-free (if taken from healthy animals), one must simply prevent contamination of the raw materials with pyrogens during purification to obtain a pyrogen-free product. Pyrogen-free buffers and solid phases are used in affinity chromatography columns to obtain pyrogen-free polyclonal antibodies as described in Example 1 of U.S. Pat. No. 6,696,261. Alternatively, monoclonal antibodies from hybridoma cultures can be used. However, when using monoclonal antibodies, care must be taken to isolate the antibodies from any contaminating pyrogen which may be present in the hybridoma cell culture.

For use in the present invention, the antibody to the cytokine is applied to a surface in an assay system. Methods, such as coating, for binding antibodies onto a surface in an assay system, such as a microtiter well, are well known in the biochemical arts. Many assay systems are available commercially, and the manufacturer usually provides materials and instructions for coating antibodies onto a surface of the system. Because of their ease of reading and the small sample volume required, microtiter wells in which a portion of the interior surface of the well is coated by the antibody are used in a preferred embodiment of the present invention. In order to fully exploit the advantages of the invention, it is preferred that the microtiter well be part of a microtiter plate, which is a planar array of similar wells, situated so that the array of wells may be read with automated immunoassay plate reading equipment (see, e.g., U.S. Pat. No. 5,281,540, hereby incorporated by reference). Automated equipment such as ELISA plate readers (e.g., the Ultramark Microplate Reader, available from Bio-Rad Laboratories, Inc.), automate the assay evaluation process and greatly decrease the per-test cost. If desired, microtiter well plates can be rendered pyrogen-free (if not already supplied as such) by extensive washing with pyrogen-free buffer. In a particularly preferred embodiment of the present invention, anti-IL-6 polyclonal antibodies are coated onto the wells of an ELISA plate. However, other immuno-diagnostic test formats (e.g., in which the antibody is coated on a dipstick or bead) are acceptable for use in the present invention.

In addition to the "capture" antibody, other antibodies and reagents for use in assaying the cytokine may be applied when making microtiter plate systems for use in the present invention. For instance, after the capture antibody is applied to the microtiter plate, the remaining binding sites of the plate can be "blocked" with another protein. After blocking, a labeled detection antibody (such as a biotinylated or enzyme-labeled antibody) can be applied to the microtiter plate, along with a protective glazing compound. Thus, when a sample is incubated in the microtiter well, as described below, a released cytokine is captured by the capture antibody bound to the well and labeled by the detecting antibody simultaneously during the sample incubation period.

C. Monocyte-Containing Reagent

As the first step in the pyrogen tests of the present invention, cells contained within a monocyte-containing reagent are cultured by combining the monocyte-containing reagent and a sample to be tested in an assay system. The monocyte-containing reagent of the present invention is selected from the group consisting of PBMCs, monocytic cell line cells, whole blood, or any cell line that expresses or can be made to express the Toll-like receptors (TLRs) that are involved in mediating responses to pro-inflammatory and pyrogenic agents, including cells into which these receptors have been induced or cloned. Preferably, the monocytic cell line is selected from the group consisting of MONOMAC-6 (MM6), THP-1, and 28SC. The monocytes in the monocyte-containing reagent preferably are monocytes from the same species to whom the product tested is to be administered (i.e., human for pharmaceutical products; cat, dog, horse, etc. for veterinary products). However, monocytes from other species with the desired pyrogen reactivity may also be used. In certain preferred embodiments, the monocyte-containing reagent comprises PBMCs.

In one embodiment of the invention, the monocyte-containing reagent is whole blood and the assay system includes at least one surface comprising polypropylene, such that the monocyte-containing reagent is in contact with the surface.

In another embodiment, the monocyte-containing reagent is PBMCs present in high cell density, and the assay system includes at least one surface comprising polypropylene, polyethylene, polystyrene, or another similar material in contact with the PBMCs.

When the monocyte-containing reagent is PBMCs or cell line cells, the reagent is present in the assay system at a high cell density, to facilitate greater cell to cell contact, as explained above in detail. In certain embodiments, the monocyte-containing reagent is present in the assay system at a cell density per well of at least about 125,000 cells, at least about 250,000, 500,000, 600,000, 700,000, 800,000, 900,000, 1,000,000, 1,100,000, 1,200,000, 1,300,000, 1,400,000, 1,500,000, 1,600,000, 1,700,000, 1,800,000, 1,900,000 or 2,000,000 cells per well. One of ordinary skill in the art would recognize that the maximum cell density is exceeded when insufficient cell nutrients exist in the volume of reagent within the well to properly maintain the cells within the well.

When the monocyte-containing reagent is whole blood, the reagent is present in the assay system at a lower cell density than PBMCs or cell line cells. In certain embodiments where the monocyte-containing reagent is blood, the reagent is present in the assay system at a cell density of at least about 100,000 peripheral blood mononuclear cells per well, at least about 200,000, 210,000, 220,000, 230,000, 240,000, 250,000, 260,000, 270,000, 280,000, 290,000, 300,000, 310,000, 320,000, 330,000, 340,000, 350,000, 360,000, 370,000, 380,000, 390,000 or 400,000 PBMC per well. Without being bound to a particular theory, it is believed that whole blood can be used at a lower cell density as compared to PBMCs or cell line cells because monocytes are in their natural environment and all serum components which may influence their response to pyrogens are present in solution. Furthermore, when the monocyte-containing reagent comprises whole blood, the readout used for the pyrogen test is IL-6.

Preferably, when blood is used as the monocyte-containing reagent, the blood is fresh, or less than 24 hours old, and more preferably less than 4 hours old. Also, when whole blood is used, anticoagulants can be included to retard or prevent blood clotting; suitable anticoagulants include citrate (for example, to a final concentration of 0.38%), heparin (sodium heparinate), or fragmin (low molecular weight heparin). Anticoagulant additives can be used without affecting the response of the monocytes to pyrogens in the test sample. Whole blood can also be diluted with an appropriate buffer or other diluent, such as RPMI cell culture media or physiological saline. Whole blood is preferably diluted to at least 50%, more preferably to about 5% to about 25%, and more preferably about 20% of the final volume for incubation (see FIG. 1 of U.S. Pat. No. 6,696,261). By diluting whole blood, the IL-6 response curve of the majority of donors may be brought within a compact range that can be used to quantify a wider range of pyrogen contamination concentrations (see FIG. 3 of U.S. Pat. No. 6,696,261).

2. Two Assay System

In certain embodiments of the present invention, the pyrogenicity test is carried out in a two assay container system, such that the steps of sample incubation with the monocyte-containing reagent and the capture of cytokine(s) produced by the monocyte-containing reagent occur in two different assay container systems. The incubation step follows the culturing step described above; incubation of the test sample with the monocyte-containing reagent (such as PBMCs) is performed in the same assay system as the culturing step. The optimal incubation time for use in the pyrogen test of the present invention will vary depending on the assay conditions, namely the cytokine which is assayed. For example, when whole blood is incubated with endotoxin and the readout is IL-6, minimal additional cytokine is produced by the monocyte-containing reagent after incubation for 6 hours; after 4 hours of incubation, a sufficient amount of IL-6 has been secreted by the reagent to allow quantification of the pyrogen contaminant. When whole blood is incubated with non-endotoxin pyrogen and any readout is used, a sufficient amount of IL-6 has been secreted by the reagent to allow quantification of the pyrogen contaminant after about 16-24 hours of incubation. For an embodiment of the present invention which assays IL-6 production, an incubation time of about 6 to about 24 hours, more preferably about 12 to about 24 hours, and most preferably about 16 to about 24 hours is preferred. If another cytokine is assayed, the incubation period should be optimized for the production of that particular cytokine. Such optimization is within the abilities of the person of ordinary skill in the art. If the cytokine to be assayed is not released by the monocytes, the cells can be lysed by freeze thawing, or by adding a detergent at the end of the incubation period in a concentration which will not disrupt binding of ligands to antibodies.

Once the incubation step is completed, the contents of the assay system (the first assay system), namely the monocyte-containing reagent and the test sample, are transferred to a second assay system which comprises at least one surface treated with an antibody to a cytokine or an endogenous mediator of the inflammatory response, e.g., endothelin. The second assay system is assayed for the presence of cytokine or endogenous mediator on the surface coated with the anti-cytokine or anti-endogenous mediator antibody. Preferably, rigorous, sterile conditions are maintained at all points in the procedure before the antibody coated surface is assayed for bound cytokine. If an ELISA plate coated with a capture antibody is used as the embodiment of the present invention, the plate is washed, and a second anti-cytokine antibody conjugated with an enzyme is added to the ELISA plate (unless the second, labeled, "detecting" antibody was initially added to the plate before glazing or together with the contents of the first assay system). The ELISA plate is washed again, and addition of a substrate to the ELISA plate will produce a color. After a short incubation time, the reaction is terminated, and the optical density of the solution is measured on an ELISA plate reader. This process is further described in Example 2 of U.S. Pat. No. 6,696,261. Alternatively, non-enzymatic immunoassay techniques may be used. For instance, the second antibody of the immunoassay "sandwich" may be labeled with a fluorescent moiety or a radioactive isotope. After washing, the amount of cytokine captured in the well can be quantified by detecting the amount of fluorescence or radiation present in the well. Several enzymatic and non-enzymatic based assay systems are available commercially and can be easily modified for use in the present invention by one of ordinary skill in the art.

3. One Assay System

In certain embodiments of the present invention, the pyrogenicity test is carried out in a one assay container system, such that the steps of sample incubation with the monocyte-containing reagent and the capture of cytokine(s) produced by the monocyte containing reagent occur in the same assay container system. The assay system comprises at least one surface comprising polypropylene and at least one surface treated with an antibody to a cytokine or an endogenous mediator of the inflammatory response. The incubation step follows the culturing step described above and is performed in the same assay system as the culturing step. As described above in the context of the two assay container system, the optimal incubation time for use in the pyrogen test of the present invention will vary depending on the assay conditions, namely the cytokine which is assayed. Generally, the teachings regarding the incubation step discussed with respect to the two assay container system apply to the one assay container system as well. The incubation period should be optimized for the production of a particular cytokine and such optimization is within the abilities of the person of ordinary skill in the art. If the cytokine to be assayed is not released by the monocytes, the cells can be lysed by freeze thawing, or by adding a detergent at the end of the incubation period in a concentration which will not disrupt binding of ligands to antibodies.

Once the incubation step is completed, the assay system, which comprises at least one surface treated with an antibody to a cytokine or an endogenous mediator of the inflammatory response, e.g., endothelin, is assayed for the presence of cytokine or endogenous mediator on the surface coated with the anti-cytokine or anti-endogenous mediator antibody. Preferably, rigorous, sterile conditions are maintained at all points in the procedure before the antibody coated surface is assayed for bound cytokine. Generally, the discussion regarding the assaying step of the two assay container system, i.e., the discussion of the ELISA plate and non-enzymatic immunoassay techniques, apply to the one assay container system as well.

In general, the one assay container system and the two assay container system are interchangeable.

4. Assay Containers

The assay systems of the present invention comprise at least one surface in contact with the monocyte-containing reagent. In certain embodiments of the present invention the assay system(s) includes at least one microtiter well, and the surface is at least a portion of the interior of the microtiter well. In particular embodiments, the surface of the microtiter well comprises a polypropylene coating or the entire microtiter well is composed of polypropylene. In certain embodiments where the assay system comprises at least one surface treated with an antibody to a cytokine or to an endogenous mediator of the inflammatory response, the surface on which the antibody is applied is at least a portion of the interior of the microtiter well. Preferably, the microtiter well is shaped such that the monocyte-containing reagent is concentrated as compared to a flat-bottomed microtiter well.

In certain embodiments, the microtiter well(s) comprises an open top, an upper region extending downwardly from the open top, and a bottom wall tapering in diameter from a location above the lowest point to the lowest point.

In certain embodiments, the microtiter well(s) comprises an open top, an upper region extending downwardly from the open top having a top end and a bottom end, and a bottom region having a top end and a lowest point, the bottom region extending from the bottom end of the upper region and tapering in diameter more rapidly than the upper region from the top end of the bottom region toward the lowest point.

In certain embodiments, the bottom wall of said microtiter well is non-planar, preferably curved, sometimes parabolic. In certain particular embodiments, the bottom wall is downwardly extending, or the sides of the microtiter well are sloped inward.

5. Diagnostic Kit

Any one of the embodiments described above can be incorporated into a diagnostic kit for performing pyrogen tests. The kit is used to detect a variety of non-endotoxin pyrogens, including Gram-positive bacteria (e.g., *Staphylococcus aureus*) or their components (e.g., muropeptide, lipoteichoic acid, enterotoxins, streptolysin), as well as endotoxin pyrogens in a variety of medical products, including blood products or other parenterals, such as dialysates, vaccines, and intravenous solutions. Generally, such a kit includes a microtiter plate comprising a plurality of microtiter wells shaped such that culture medium contained in each well is concentrated as compared to a flat-bottomed microtiter well, the wells comprising at least one surface comprising polypropylene. The wells of the microtiter plate contain cryopreserved monocyte-containing reagent comprising cryopreserved whole blood, cryopreserved peripheral blood mononuclear cells or cryopreserved monocytic cell line cells, which are in contact with the surfaces of the wells. In certain embodiments, the wells of the microtiter plate comprise polypropylene. When the cryopreserved monocyte-containing reagent comprises cryopreserved peripheral blood mononuclear cells or cryopreserved monocytic cell line cells, the reagent is present in the wells at a high cell density. Kits containing cryopreserved whole blood as the monocyte-containing reagent also contain antibody to IL-6, as IL-6 is the preferred readout.

In particular embodiments, the wells include a barrier which is impervious to monocytes. The barrier comprises at least one surface comprised of a pyrogen-free material, and is typically a membrane, a grid, a sieve, or a sifter. The barrier is preferably sterile. Suitable barrier materials for use with microtiter plates are known in the art. The barrier, which is permeable to fluids, allows cryopreserved cells to be washed without being removed from the wells; dimethyl sulfoxide (DMSO), which bathes cryopreserved cells and acts as a preservative, can be removed so that it does not interfere with the testing. Test samples are added above the barrier, penetrate the barrier, contact cells below the barrier, and potentially stimulate these cells to produce cytokines. Cytokines released by cells diffuse into the medium above the barrier. Typically, the solutions above and below the barrier are thoroughly mixed, by aspirating the solutions. Subsequently, an aliquot of well-mixed medium from above the barrier is assayed for the presence of cytokine or an endogenous mediator of the inflammatory response.

6. Interpretation of Cytokine Production Data

A. Standard Curve Method

In order to properly interpret the cytokine production data generated in the pyrogen test of the present invention, an endotoxin standard curve is generated by incubating the monocyte-containing reagent with USP standard endotoxin. The purpose of this is to quantify the cytokine production response measured for a test sample in terms of the response observed for a known pyrogen. A standard curve may be generated from any statistically significant number of data points generated with significantly varied concentrations of standard endotoxin by utilizing standard best-fit data analysis software. Methods of generating such standard curves are generally known in the art. Applicants have found that data points of 10, 4, 1, 0.25, 0.06, 0.03, and 0 EU/ml of endotoxin are suitable for generating a standard curve, but any statistically significant number of concentrations through a similar range would be suitable. Once a standard curve is generated, the equivalent non-endotoxin concentration (quantified in endotoxin unit-equivalents) may be interpolated from the cytokine response using the standard curve. As the response of whole blood-based monocyte-containing reagents can vary significantly from donor to donor, it is important to generate a standard curve for each set of assays performed with a particular lot of monocyte-containing reagent. However, because the preferred ELISA plate embodiment of the invention utilizes very small amounts of human blood (about 40 µL/well), a single unit of donated blood can be used for several hundred wells. The standard curve generated using the USP endotoxin aids in the normalization of the data in terms of relating to endotoxin units (EU, as defined by the USP/FDA, which are identical to IU, international units as defined by WHO), which is the industry standard for expressing endotoxin/pyrogen contamination.

B. Reference Lot Method

Alternatively, the cytokine production data generated in the pyrogen test of the present invention may be interpreted by comparing cytokine responses elicited by test lots of a product to those elicited by reference lots of a product, a contaminated reference lot and an uncontaminated reference lot. First, the two reference lots of a medical product are identified: the reference lots are pyrogen tested and the cytokine responses elicited by these lots are measured. Then, test lots are pyrogen tested and the responses elicited from these lots are compared to those of the reference lots. Generally, a test lot will be deemed uncontaminated if it elicits a lesser response than the contaminated reference lot and a response similar to that of the uncontaminated reference lot. Each test lot may be tested once or several times. For example, according to one reference lot method, a product was deemed uncontaminated if it elicited the release of no more than two times as much IL-6 as the uncontaminated reference lot in four out of four donors or seven out of eight donors; the test was conducted in quadruplicate using the blood of four different donors. A preferred reference lot method is described in Gaines-Das et al., 2004, in which the test sample is required to stimulate the release of less IL-6 than the reference. In that article, the test preparation is required to pass the test with the PBMNC from four different donors. If the test preparation passes the test with the PBMNC from three of the four donors, the test is continued with PBMNC from a further four donors, none of whom provided PBMNC for the first test, and the test preparation is required to pass the test with the PBMNC from seven of the eight different donors.

Advantageously, the monocyte activation tests of the present invention are better able to detect the presence of a wide variety of pyrogens, including non-endotoxin pyrogens, in medical products such as blood products, intravenous solutions, and vaccines.

DEFINITIONS

As used herein, the term "pure" endotoxin or non-endotoxin pyrogen or pyrogen in its "pure form," refers to endotoxin that has been stripped of its associated protein. Pure endotoxin is also known as lipopolysaccharide (LPS).

The term "monocyte-containing reagent" means any solution of monocytic leukocyte cells of the immune system. Preferably, these cells are derived from the organism to whom the product which is being tested is to be administered (i.e., human for pharmaceutical products, cat, dog, horse, etc. for veterinary products). An example of a monocyte-containing reagent is whole human blood.

The term "assay system" means any container and surface which may be used in a monocyte activation test, including a container in which cells are cultured and incubated with a test sample as well as a container and surface with bound antibody which may be used in an immunoassay. Preferably, with regard to performing an immunoassay, such containers are microtiter well plates with antibody bound to a surface in the well, in which a large number of colorimetric enzyme-linked immunoassays may be carried out in parallel and which may be automatically evaluated by an ELISA plate reading machine. However, other immunoassay systems are envisioned, especially those where the coated surface is not necessarily part of the wall of the container. For instance, a larger test tube which contains a polystyrene bead or dipstick coated by the antibody could be used in the present invention.

The term "monocytic cell line" includes any cell line that has endogenous CD14 and/or Toll-like receptors (TLRs) or which has been transfected with CD14 and/or TLRs and/or reporter genes for inflammatory/pyrogenic mediators. The cell line does not have to be monocytic provided it has or has been transfected with the components of the "pyrogen receptors" present on monocytes: these components include TLRs and CD14. For example, Human Embryonic Kidney (HEK) cells already have most of the TLRs and can be stably transfected with the TLRs that they do not have—TLR2 and TLR4—and also CD14 to make them sufficiently like a monocyte to function in the methods of the invention.

EXAMPLES

Example 1

Preparation of PBMC

PBMCs were isolated from human heparinized peripheral blood that was not more than 4 hours old by density-gradient centrifugation using Ficoll Paque Plus (Pharmacia #17-1440-02). The cells were washed twice with Dulbecco's phosphate buffered saline without calcium and magnesium (Gibco #14190), re-suspended in Minimum Essential Media (MEM) (Gibco #11090), HEPES buffer (Gibco #15630), and 5 µL of the donors own heat-inactivated plasma (i.e., 2% of final concentration). The PBMCs were diluted to the required cell densities (8 million, 4 million, 2 million, and 1 million PBMCs per mL).

Cell Culturing.

Cell cultures were carried out in quadruplicate on the following microtiter plates: Corning Costar #3790, #3359. 125 µL of cell suspension containing 1 million, 0.5 million, 0.25 million, or 0.13 million cells was added to each well, followed by 125 µL of test sample or standard endotoxin (0.0064-20 EU/mL). The 250 µL mixture was gently mixed and incubated at 37±1° C., in 5% $CO_2$ and in humidified air. The duration of the culture was 16 to 24 hours, after which time aliquots of the culture fluid were obtained, diluted 1 in 2 and 1 in 50, and assayed for IL-6.

ELISA for IL-6.

96-well plates (Immulon 4, Dynex #011-010-3855) were coated with 150 µL of 3 µg/mL mouse monoclonal IgG (R&D Systems #MAB206 dissolved in bicarbonate buffer, pH 9.5) by incubation overnight at 2-8° C. The plates were washed three times with 300 µL wash buffer (20 mM HEPES, 150 mM NaCl, pH 7.4). Non-specific binding sites on the plates were blocked by adding 200 µL of blocking solution (0.02 g/L Bovine Serum Albumin, Fraction V, protease-free). The plates were again washed three times with 300 µL of the same wash buffer, and 100 µL of samples (previously diluted 1 in 2 and 1 in 50 in sample diluent) or standards (7.8-1000 pg/mL of WHO international standard for IL-6, #89/548) were added to each well. 100 µL of sample diluent was added to each unused well. The plate was covered with sealer (Falcon #3073) and incubated with shaking (approximately 300 rpm) for 1 hour±5 minutes.

The plate was then aspirated and washed five times with 300 µL of wash buffer. Then, 100 µL of 0.2 µg/mL biotinylated goat anti-human IL-6 antibody (R&D Systems, #BAF206) was added to each well and the plate was again covered with sealer and incubated with shaking (approximately 300 rpm) for 1 hour±5 minutes.

The plate was then aspirated and washed five times with 300 µL of wash buffer. Then, 100 µL of 0.02 µg/mL alkaline phosphatase (Rockland #S000-05) was added to each well and the plate was again covered with sealer and incubated with shaking (approximately 300 rpm) for 1 hour±5 minutes.

The plate was aspirated and washed five times with 300 µL of wash buffer. Then, 200 µL of 1 mg/mL pNPP in diethanolamine buffer with 0.5 mM $MgCl_2$ was added to each well. The plate was again covered with sealer and incubated with shaking (approximately 300 rpm) at room temperature until the largest concentration of the IL-6 standard curve (1000 pg/mL) had an optical density between about 2.5 and 3.0 at 405 nm, at which point the reaction was stopped by adding 50 µL of 2M NaOH to each well. The optical density of each well was determined within 30 minutes of the reaction being stopped using a microplate reader set to 405 nm.

FIG. 1 shows the effect of cell density on the IL-6 responses to endotoxin standard (1 EU/ml) and Extraneal® positive control. The Extraneal® positive control was contaminated with non-endotoxin pyrogen and caused an adverse drug reaction in human recipients of this lot of this drug but gave a negative response in the LAL test (Martis et al. 2005). Values are means±standard error of the means of four replicate wells. Cell densities of 0.25 to 1 million PBMC per well responded similarly to the 1 EU/ml endotoxin standard. The positive control sample was best detected using 1 million>0.5 million>0.25 million>>0.13 million cells per well.

Example 2

Comparative Pyrogen Tests

The methods described herein as the current state of the art were replicated. None of these methods discriminate positive product controls for Extraneal® dialysis solution, hemoglobin and/or dextran from negative product controls.

Figure 6:
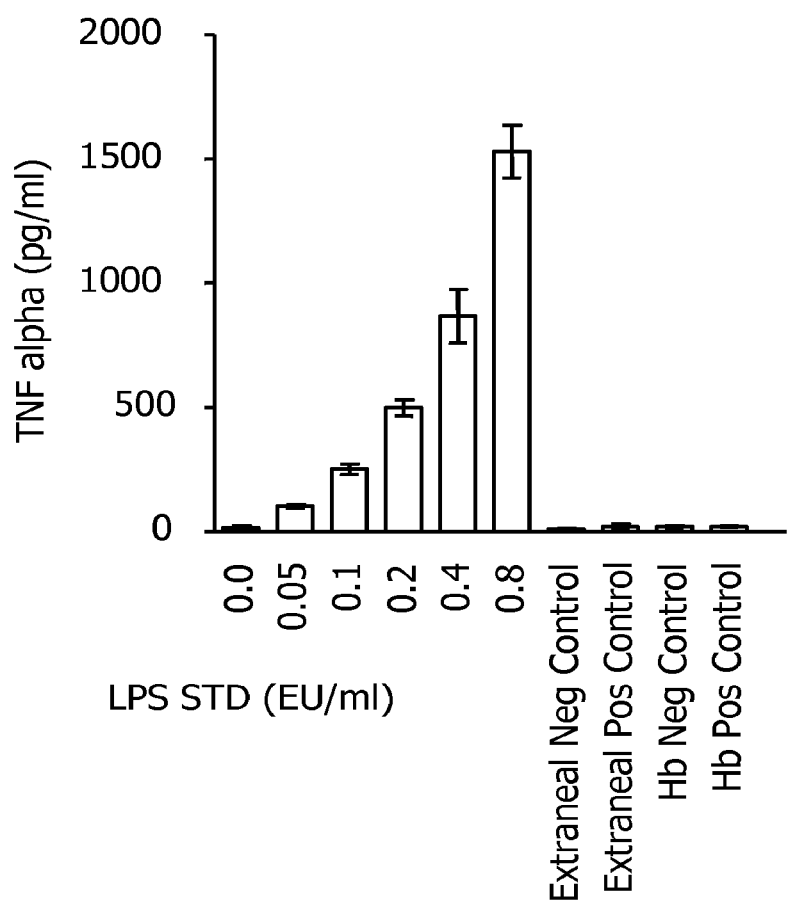
FIG. 6 is a graph illustrating TNF-α responses for test samples having low cell density in a monocyte activation test carried out with THP-12A9 cells on polystyrene plates with flat-bottomed wells. TNF-α responses are to LPS, Extraneal® positive and negative controls and Hb positive and negative controls.
Figure 7:
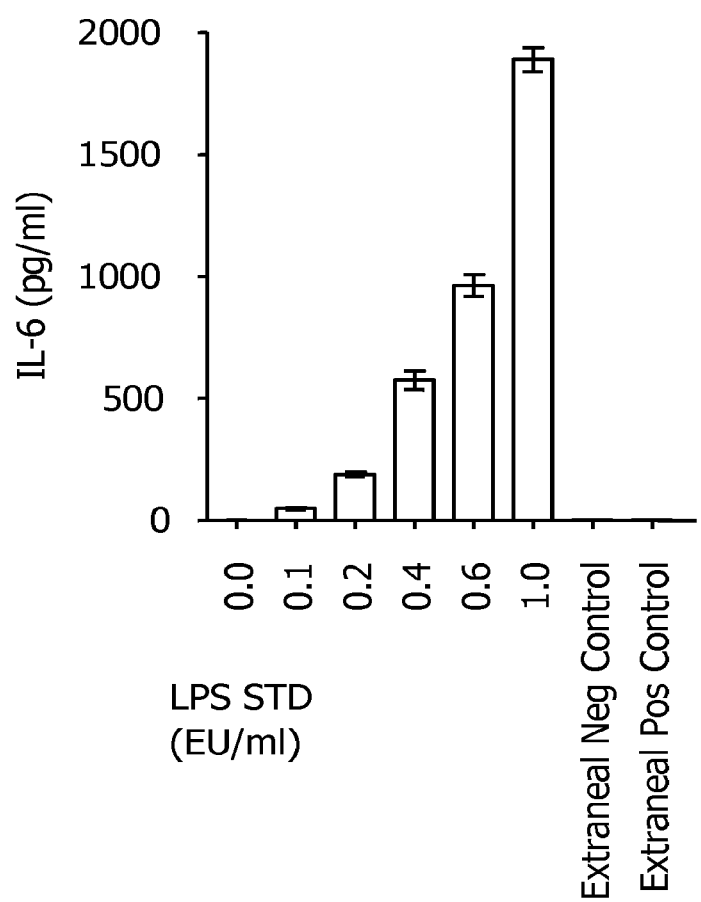
FIG. 7 is a graph illustrating IL-6 responses for test samples having low cell density in a monocyte activation test carried out with MONOMAC6-CA8 clone cells on polystyrene plates with flat-bottomed wells. IL-6 responses are to LPS, and Extraneal® positive and negative controls.
Figure 8:
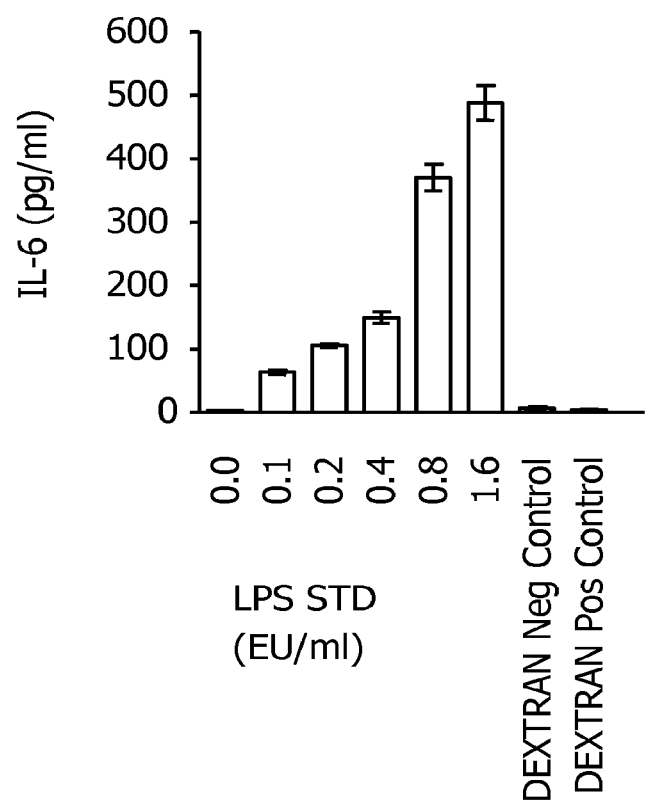
FIG. 8 is a graph illustrating IL-6 responses for test samples having low cell density in a monocyte activation test carried out with 28SC cells on polystyrene plates with flat-bottomed wells. IL-6 responses are to LPS and dextran positive and negative controls.

The assays of Hoffman et al., 2005 were replicated as described therein using polystyrene microtiter plates with flat-bottomed wells and IL-6 readout. The monocyte-containing reagent was used in low cell density and was whole blood (75,000 cells per well), PBMCs (100,000 cells per well), MONOMAC6 (250,000 cells per well), or THP-1 (250,000 cells per well) in FIGS. 2-5, respectively. Note that in FIG. 5, IL-6 readout was substituted for neopterin because IL-6 is an endogenous pyrogen (in contrast to neopterin) and a more robust readout in the methods of the invention. In FIG. 6, THP-12A9 cells in low cell density (250,000 cells per well) were used as the monocyte-containing reagent and TNF was the readout.

The assay of Nakagawa et al. was replicated as described therein using 1,000,000 MONOMAC-CA8 clone cells per ml as the monocyte-containing reagent, IL-6 readout, and polystyrene microtiter plates with flat-bottomed wells. See FIG. 7.

The assay of Yamamoto et al. was replicated as described therein using 1,000,000 28 C cells per ml as the monocyte-containing reagent, IL-6 readout, and polystyrene microtiter plates with flat-bottomed wells. See FIG. 8. However, the 28 C cells were primed with calcitriol (100 ng/nl) rather than interferon gamma because the latter failed to give a dose-response curve to endotoxin standard.

Example 3

Pyrogen Test of the Invention

Cultures (200 µl) of 20% human whole blood (40 µl=approx 60,000 PBMC/well=approx. 300,000 PBMC/ml) were carried out in quadruplicate on 96-well round-bottomed polypropylene plates (Costar #3790, Corning Incorporated, USA). The additions per well were: MEM-HEPES (60 µl), blood from a single donor (40 µl), endotoxin standard or Extraneal® samples diluted 1:1 with MEM-HEPES (100 µl, i.e. the Extraneal® solution was at a final dilution of 1 in 4 in the well). The contents of the wells were mixed by swirling gently (without cross-contaminating wells) and incubated without vibration (to allow the cells to settle) at 37° C. for 16-24 h in an atmosphere of 5% $CO_2$ in air. At the end of the tissue culture incubation, 100 µl aliquots of clear supernatant from each well were taken for assay of IL-6 by ELISA.

The methodology used for the dextran samples was similar to that described above in Example 1. The cell isolation and culture were similar, except that the cell density was 400,000 cells per well and the sample dilution used in the ELISA was 1 in 10. The IL-6 ELISA was different in that it used plates coated with Clone16 monoclonal antibody (for capture of IL-6) and a sheep polyclonal antibody conjugated to horse-radish peroxidase as the detecting antibody. The ELISA is used in the whole blood/IL-6 test (NIBSC) and the PBMC/IL-6 test (Novartis) as described in the Hoffmann et al. paper, 2005.

FIG. 9 illustrates comparative results for the Extraneal® negative control sample and the Extraneal® positive control sample, and for dextran negative control sample and dextran positive control sample. It can be seen that the pyrogen test of the invention can readily discriminate between these positive and negative controls. The test was carried out, in quadruplicate, according to the protocol described above, with blood from a single donor. Values are means±standard error of the means of four replicate wells.

Figure 10:
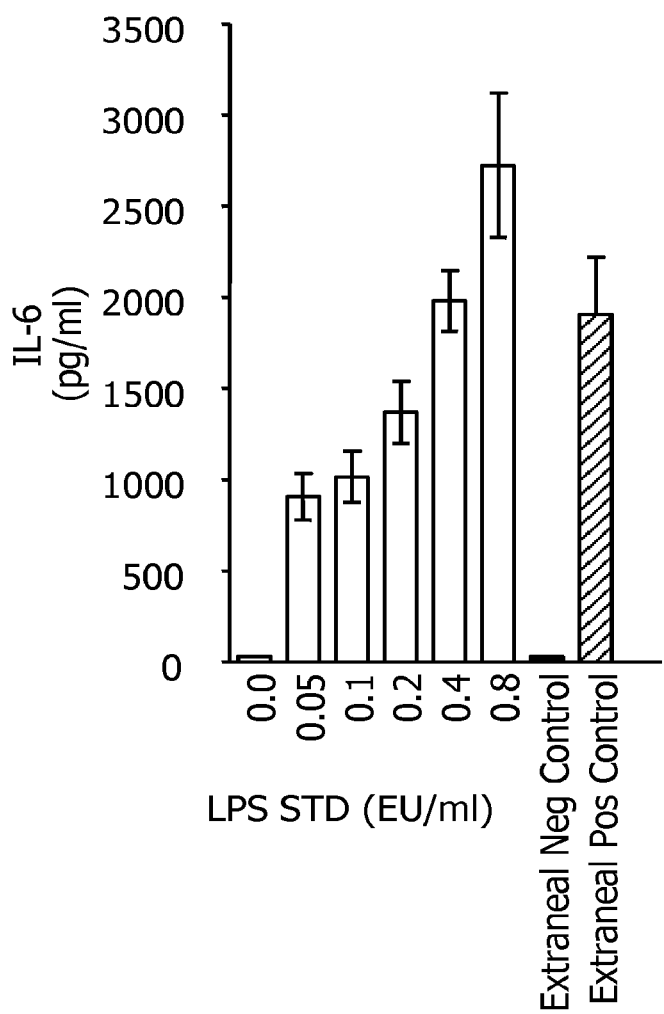
FIG. 10 is a graph depicting IL-6 responses for test samples having low cell density in a monocyte activation test carried out with whole blood on polypropylene plates with round-bottomed wells. IL-6 responses are to LPS, and Extraneal® positive and negative controls.

FIG. 10 illustrates comparative results for the Extraneal® negative control sample and the Extraneal® positive control sample. It can be seen that the pyrogen test of the invention can readily discriminate between these positive and negative controls. The test was carried out, in quadruplicate, according to the protocol described above, with blood from a single donor. Values are means±standard error of the means of four replicate wells. Note that low cell density was sufficient for discrimination of positive from negative Extraneal controls when whole blood was the monocyte-containing reagent and round-bottomed polypropylene wells were used.

Example 4

Figure 11A:
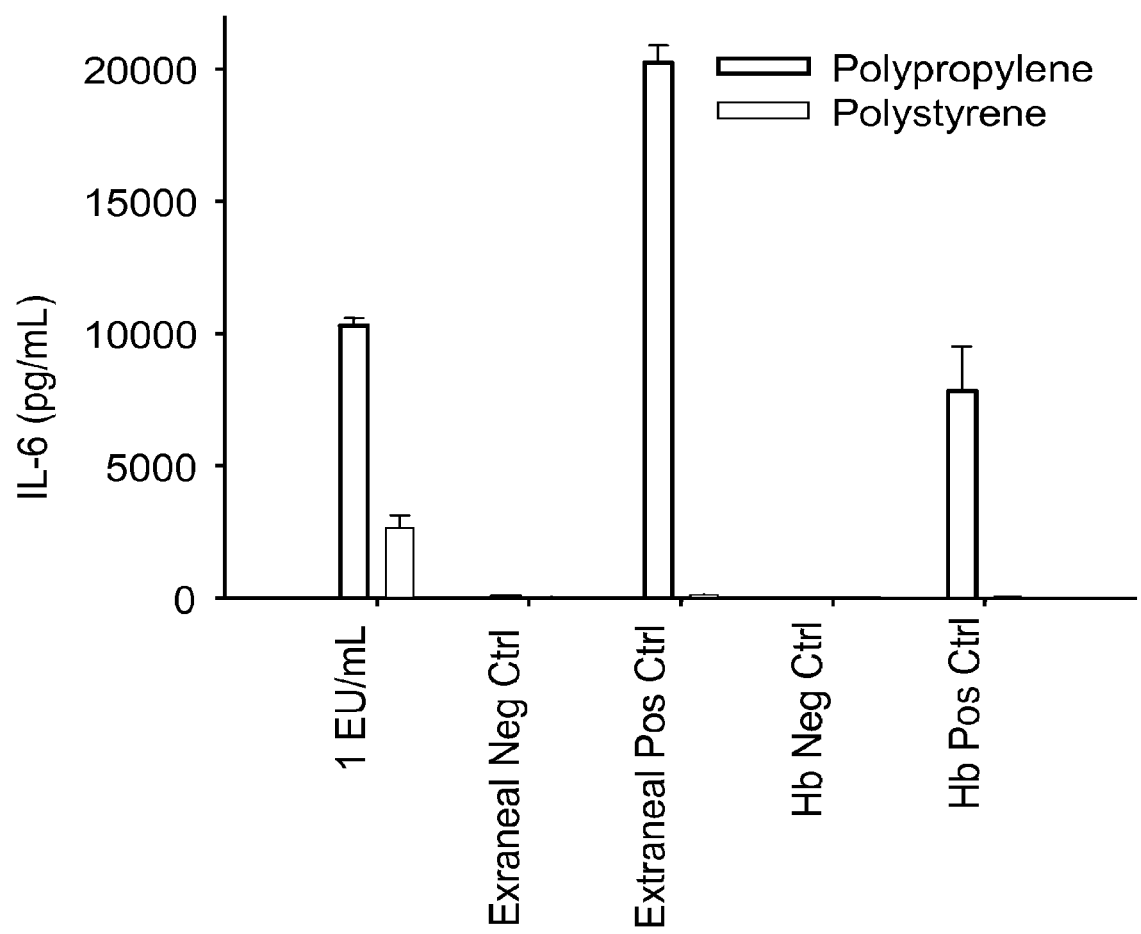
FIG. 11A is a graph depicting IL-6 responses for polypropylene plates (black columns) and polystyrene plates (grey columns) in a monocyte activation test carried out with peripheral blood mononuclear cells (1 million cells per well). IL-6 responses are to LPS, Extraneal® positive and negative controls and Hb positive and negative controls.
Figure 11B:
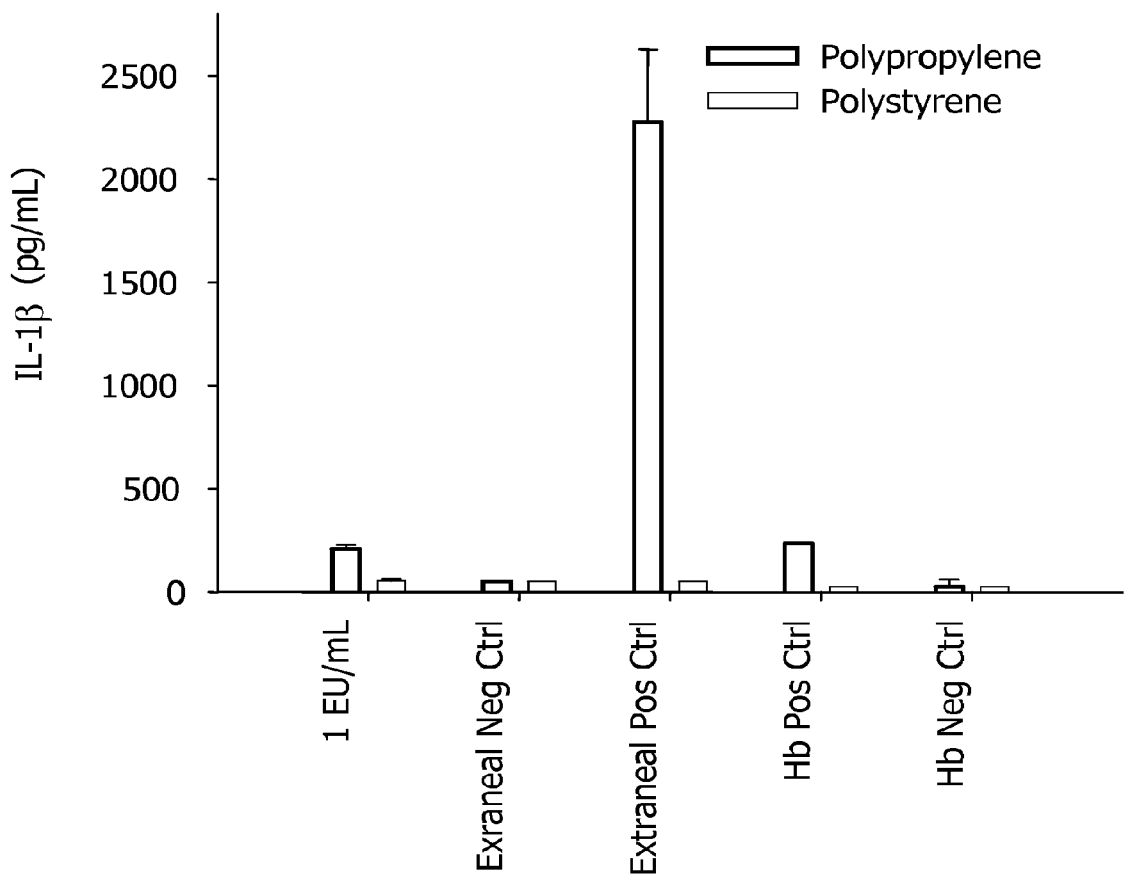
FIG. 11B is a graph depicting IL-1β responses for polypropylene plates (black columns) and polystyrene plates (grey columns) in a monocyte activation test carried out with peripheral blood mononuclear cells (1 million cells per well). IL-1β responses are to LPS, Extraneal® positive and negative controls and Hb positive and negative controls.

Pyrogen Test of the Invention: Comparative Results for Polypropylene Plates Vs. Polystyrene Plates and IL-6 vs. IL-1β for a Single Donor The test samples were prepared according to the method of Example 1, except that cell densities of 1 million cells per well were used, some samples were subjected to IL-1β readout, and some samples were placed in polystyrene microtiter plates with flat-bottomed wells. FIG. 11A shows that IL-6 responses to positive controls were clearly distinguished from negative controls for tests conducted in polypropylene plates, but were not distinguished for those in polystyrene plates. Values are means±standard error of the means of four replicate wells. FIG. 11B shows that IL-1β responses to positive controls were clearly distinguished from negative controls for tests conducted in polypropylene plates, but were not distinguished for those in polystyrene plates. However, the magnitude of the response in FIG. 11B was much less than that of FIG. 11A, indicating that IL-1β is a poor readout as compared to IL-6. Values are means±standard error of the means of four replicate wells.

Example 5

Figure 12A:
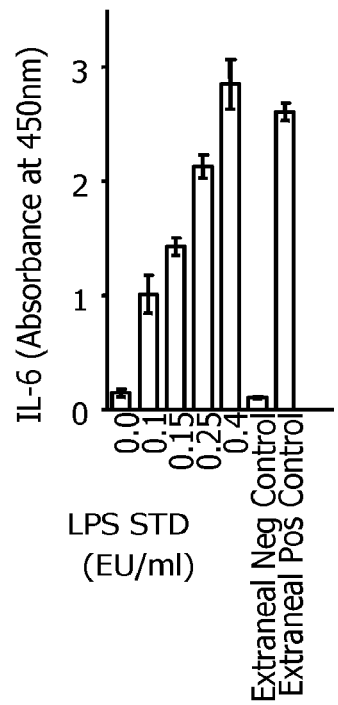
FIG. 12A is a graph illustrating IL-6 responses for test samples having high cell density in a monocyte activation test carried out with peripheral blood mononuclear cells on polypropylene plates with round-bottomed wells. IL-6 responses are to LPS and Extraneal® positive and negative controls.
Figure 12B:
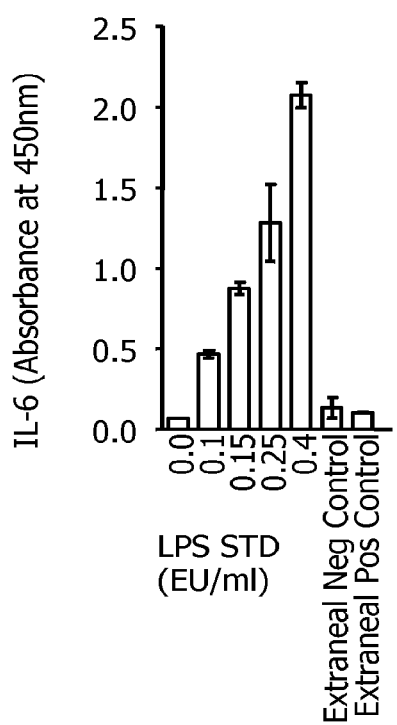
FIG. 12B is a graph illustrating IL-6 responses for test samples having low cell density in a monocyte activation test carried out with peripheral blood mononuclear cells on polystyrene plates with flat-bottomed wells. IL-6 responses are to LPS and Extraneal® positive and negative controls.
Figure 13A:
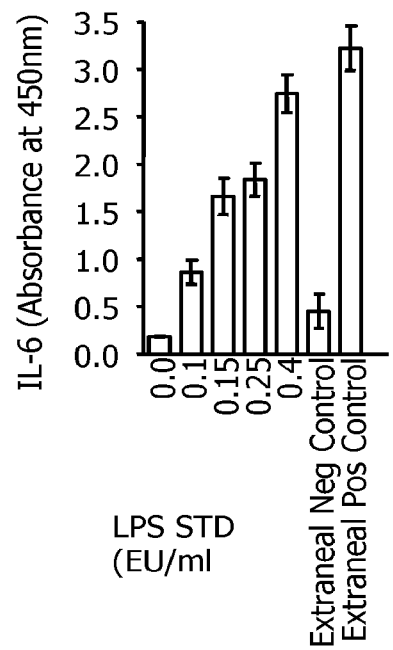
FIG. 13A is a graph illustrating IL-6 responses for test samples having high cell density in a monocyte activation test carried out with peripheral blood mononuclear cells on polypropylene plates with round-bottomed wells. IL-6 responses are to LPS and Extraneal® positive and negative controls.
Figure 13B:
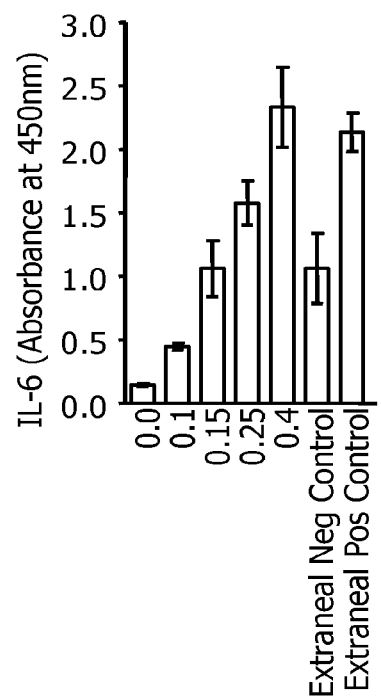
FIG. 13B is a graph illustrating IL-6 responses for test samples having high cell density in a monocyte activation test carried out with peripheral blood mononuclear cells on polystyrene plates with flat-bottomed wells. IL-6 responses are to LPS and Extraneal® positive and negative controls.
Figure 14A:
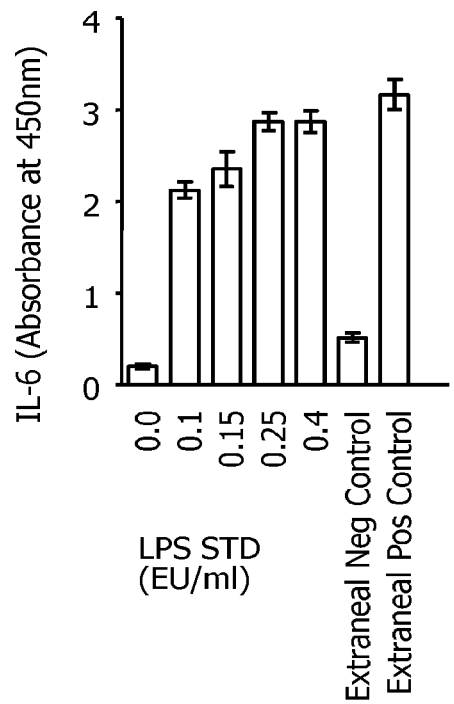
FIG. 14A is a graph illustrating IL-6 responses for test samples having high cell density in a monocyte activation test carried out with peripheral blood mononuclear cells on polypropylene plates with round-bottomed wells. IL-6 responses are to LPS and Extraneal® positive and negative controls.
Figure 14B:
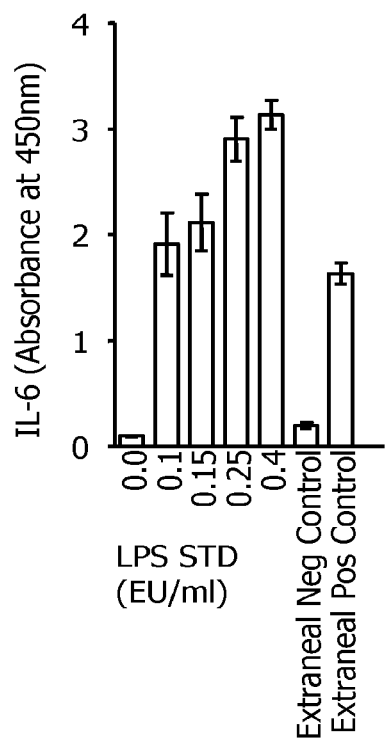
FIG. 14B is a graph illustrating IL-6 responses for test samples having high cell density in a monocyte activation test carried out with peripheral blood mononuclear cells on polystyrene plates with flat-bottomed wells. IL-6 responses are to LPS and Extraneal® positive and negative controls.

Pyrogen Test of the Invention: Comparative Results for Polypropylene Plates Vs. Polystyrene Plates for Multiple Donors The test samples were prepared according to the method of Example 1, except that cell densities of 0.88 and 1 million cells per well were used, three donors were used, some samples were placed in polystyrene microtiter plates with flat-bottomed wells, and the IL-6 ELISA used plates coated with Clone16 monoclonal antibody and a sheep polyclonal antibody conjugated to horse-radish peroxidase as the detecting antibody as described in the Hoffmann et al. paper, 2005. FIGS. 12A and 12B illustrate the IL-6 response for polypropylene microtiter plates with round-bottomed wells and polystyrene microtiter plates with flat-bottomed wells for PBMC cell density of 0.88 million cells per well for donor A, respectively. For donor A, the pyrogen test did not distinguish between positive and negative controls when the polystyrene plates were used, but did distinguish between these controls when polypropylene plates were used. FIGS. 13A and 13B illustrate the IL-6 response for polypropylene microtiter plates with round-bottomed wells and polystyrene microtiter plates with flat-bottomed wells for PBMC cell density of 1 million cells per well for donor B, respectively. Although both pyrogen tests distinguished between positive and negative controls for donor B, the IL-6 response for the positive control was about 6 times that of the negative control using the polypropylene plates, but only about 2 times that of the negative control using polystyrene plates. FIGS. 14A and 14B illustrate the IL-6 response for polypropylene microtiter plates with round-bottomed wells and polystyrene microtiter plates with flat-bottomed wells for PBMC cell density of 0.88 million cells per well for donor C, respectively. Although both pyrogen tests distinguished between positive and negative controls for donor B, the IL-6 response for the positive control was about twice as great using the polypropylene plates versus the polystyrene plates. Note that in polypropylene the response to the Extraneal® positive control exceeds the response to the largest dose of LPS standard, i.e. 0.4 EU/ml, whereas in polystyrene the response to the Extraneal® positive control is smaller than the response to the smallest dose of LPS standard, i.e. 0.1 EU/ml.

Example 6

Comparative Pyrogen Test: IPT (Charles River Laboratories)

Figure 15:
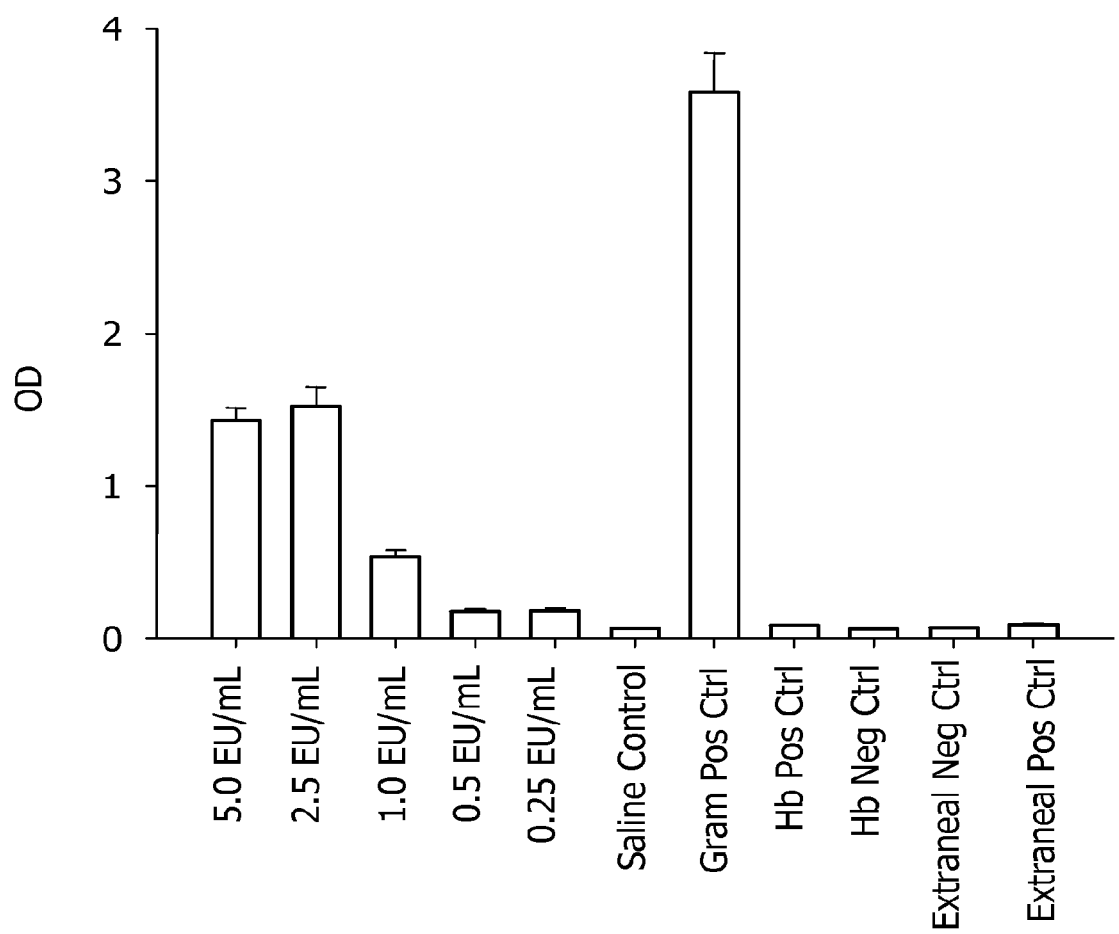
FIG. 15 is a graph illustrating IL-1β responses for test samples having high cell density in a commercially available IPT test carried out with whole blood on polystyrene plates with flat-bottomed wells. IL-1β responses are to LPS, Extraneal® positive and negative controls, hemoglobin positive and negative controls, saline control and gram positive control.

The methodology used in performing this test is described in the Endosafe®-IPT InVitro Pyrogen Test instruction sheet (commercially available from Charles River Laboratories (PIIPT10002)) using the assay procedure for whole blood stimulation using IL-1β and polystyrene microtiter plates. FIG. 15 illustrates that the IPT test failed to discriminate between Extraneal® and Hemoglobin positive and negative controls, though the kit responded to LPS standard and to a kit positive control of lipotechoic acid from a Gram-positive bacteria.

Example 7

Pyrogen Test of the Invention Using Cryo-Preserved Cells

Cell suspension (e.g. 1 million PBMC or monocytic cells) in plasma and dimethyl sulphoxide (or in whole blood and dimethyl sulphoxide) is added to each well of a 96-well polypropylene plate with round-bottomed 250 μL wells, which is then sealed and cryo-preserved.

On the day of the test, the plate is thawed, brought to room temperature, the seal removed and the 96-well insert pushed firmly into position. The insert has walls of polypropylene and a flat bottom that is a barrier to the passage of cells but not liquids.

The DMSO is washed away from the cells by filling the insert with fresh medium and aspirating the medium up and down to mix the solutions above and below the cell-barrier before aspirating and discarding the solution above the cell-barrier. By repeating this washing step 5 times, the cells are washed essentially free of DMSO and are retained in a known volume of fresh medium.

Test sample or standard and more fresh medium are added to the insert and, by aspirating this solution up and down to mix the solutions above and below the cell-barrier, pyrogen in the sample or (pyrogen) standard is allowed access to the cells.

The plate is incubated at 37±1° C., in 5% carbon dioxide gas in humidified air for 16-24 hours. During the incubation, the cells settle allowing cells to contact each other which facilitates pyrogen-stimulated IL-6 release. At the end of the incubation period, the solutions above and below the cell-barrier are thoroughly mixed by aspirating the solution above the cell-barrier up and down, before an aliquot of cell-conditioned medium is taken for assay of IL-6.

Cryo-preserved PBMCs are advantageous because they can be easily shipped on dry ice throughout the world. Unlike polystyrene, polypropylene withstands liquid nitrogen without cracking. On arrival, the PBMCs need only to be thawed and washed free of the DMSO to be ready for use in a test, in conjunction with the provided plate insert. By shipping the cells at the optimum number per well and using the cells in conjunction with the plate insert, an improved test kit is provided to the end-user. With a conventional kit, cells are shipped in a tube and, once thawed, have to be washed by centrifugation, which pellets the cells, allowing them to be dispersed in clean medium. Usually cells are washed two or three times in this way. Then the cells have to be counted and re-suspended at the required cell density before they can be dispensed into wells. The pyrogen test of the present invention is less labor intensive, less time-consuming and far less traumatic to the cells as compared to conventional tests which can result in cell loss, activation and cell death.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements. As various changes could be made in the above methods and compositions without departing from the scope of the invention, it is intended that all matter contained in the above description shall be interpreted as illustrative and not in a limiting sense.

What is claimed is:

1. A method of detecting non-endotoxin pyrogens in a sample comprising the steps of:
   (a) combining a monocyte-containing reagent and the sample to be tested in an assay system which includes at least one microtiter well shaped such that the monocyte-containing reagent is concentrated to provide greater cell to cell contact as compared to a flat-bottomed microtiter well, wherein the surface of the microtiter well comprises a polypropylene coating or the entire microtiter well is composed of polypropylene;
   (b) incubating the monocyte-containing reagent and the sample, wherein, when the sample comprises a pyrogen, the monocyte-containing reagent produces a cytokine or an endogenous mediator of the inflammatory response;
   (c) adding an antibody to the cytokine or endogenous mediator of the inflammatory response to the assay system; and
   (d) assaying the assay system for the presence of cytokine or endogenous mediator bound to the antibody;
   whereby an elevated level of cytokine or endogenous mediator bound to the surface indicates the presence of the pyrogens in the sample tested.

2. The method of claim 1, comprising adding one or more beads or dipsticks coated with the antibody to the assay system.

3. The method of claim 1, comprising adding a detection antibody to the assay system.

4. The method of claim 1, wherein the cytokine is selected from the group consisting of interleukin-1 (IL-1), interleukin-1ra (IL-1ra), interleukin-6 (IL-6), interleukin-8 (IL-8), and tumor necrosis factor-α (TNF-α).

5. The method of claim 1, wherein the monocyte-containing reagent is PBMCs, cell line cells, or whole blood.

6. A method of detecting non-endotoxin pyrogens in a sample comprising the steps of:
   (a) combining a monocyte-containing reagent and the sample to be tested in a first assay system which includes at least one microtiter well shaped such that the monocyte-containing reagent is concentrated to provide greater cell to cell contact as compared to a flat-bottomed microtiter well, wherein the surface of the microtiter well comprises a polypropylene coating or the entire microtiter well is composed of polypropylene;
   (b) incubating the monocyte-containing reagent and the sample, wherein, when the sample comprises a pyrogen, the monocyte-containing reagent produces a cytokine or an endogenous mediator of the inflammatory response;
   (c) transferring the contents of the first assay system to a second assay system which comprises an antibody to the cytokine or endogenous mediator of the inflammatory response; and
   (d) assaying the assay system for the presence of cytokine or endogenous mediator bound to the antibody;
   whereby an elevated level of cytokine or endogenous mediator bound to the surface indicates the presence of the pyrogens in the sample tested.

7. The method of claim 6, comprising adding a bead or dipstick coated with the antibody to the assay system.

8. The method of claim 6, comprising adding a detection antibody to the assay system.

9. The method of claim 6, wherein the cytokine is selected from the group consisting of interleukin-1 (IL-1), interleukin-1ra (IL-1ra), interleukin-6 (IL-6), interleukin-8 (IL-8), and tumor necrosis factor-α (TNF-α).

10. The method of claim 6, wherein the monocyte-containing reagent is PBMCs, cell line cells, or whole blood.

11. A method of testing a sample comprising the steps of:
    (a) combining a monocyte-containing reagent and the sample to be tested in an assay system which includes at least one microtiter well shaped such that the monocyte-containing reagent is concentrated to provide greater cell to cell contact as compared to a flat-bottomed microtiter well, wherein the surface of the microtiter well comprises a polypropylene coating or the entire microtiter well is composed of polypropylene;
    (b) incubating the monocyte-containing reagent and the sample,
    (c) adding an antibody to a cytokine or endogenous mediator of the inflammatory response to the assay system; and
    (d) assaying the assay system for the presence of cytokine or endogenous mediator bound to the antibody;
    whereby the sample is tested.

12. The method of claim 11, comprising adding a bead or dipstick coated with the antibody to the assay system.

13. The method of claim 11, comprising adding a detection antibody to the assay system.

14. The method of claim 11, wherein the cytokine is selected from the group consisting of interleukin-1 (IL-1), interleukin-1ra (IL-1ra), interleukin-6 (IL-6), interleukin-8 (IL-8), and tumor necrosis factor-α (TNF-α).

15. The method of claim 11, wherein the monocyte-containing reagent is PBMCs, cell line cells, or whole blood.

16. A method of testing a sample comprising the steps of:
(a) combining a monocyte-containing reagent and the sample to be tested in a first assay system which includes at least one microtiter well shaped such that the monocyte-containing reagent is concentrated to provide greater cell to cell contact as compared to a flat-bottomed microtiter well, wherein the surface of the microtiter well comprises a polypropylene coating or the entire microtiter well is composed of polypropylene;
(b) incubating the monocyte-containing reagent and the sample,
(c) transferring the contents of the first assay system to a second assay system which comprises an antibody to the cytokine or endogenous mediator of the inflammatory response; and
(d) assaying the assay system for the presence of cytokine or endogenous mediator bound to the antibody;
whereby the sample is tested.

17. The method of claim 16, comprising adding one or more beads or dipsticks coated with the antibody to the assay system.

18. The method of claim 16, comprising adding a detection antibody to the assay system.

19. The method of claim 18, wherein the detection antibody is an IL-6 antibody added to the second assay system.

20. The method of claim 16, wherein the cytokine is selected from the group consisting of interleukin-1 (IL-1), interleukin-1ra (IL-1ra), interleukin-6 (IL-6), interleukin-8 (IL-8), and tumor necrosis factor-$\alpha$ (TNF-$\alpha$).

21. The method of claim 16, wherein the monocyte-containing reagent is PBMCs, cell line cells, or whole blood.

22. The method of claim 16, wherein (i) the monocyte-containing reagent is PBMCs, (ii) the cytokine is IL-6, (iii) the antibody is an anti-IL-6 antibody, (iv) the assay system is a microtiter plate, (v) wherein the method comprises an ELISA, or (vi) a combination thereof.

23. The method of claim 16, wherein the detection antibody is an anti-IL-6 antibody.

24. The method of claim 16, wherein (i) the second assay system is a microtiter plate, (ii) the antibody is an anti-IL-6 antibody, or (iii) a combination thereof.

* * * * *